United States Patent
Katzlinger et al.

(10) Patent No.: US 8,968,658 B2
(45) Date of Patent: *Mar. 3, 2015

(54) LUMINESCENCE MEASUREMENT UTILIZING CARTRIDGE WITH INTEGRATED DETECTOR

(75) Inventors: Michael Katzlinger, Eugendorf (AT); Josef J. Atzler, Hallein (AT); Daniel M. Stock, Hallein (AT)

(73) Assignee: Molecular Devices, LLC, Sunnyvale, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 13/311,164

(22) Filed: Dec. 5, 2011

(65) Prior Publication Data

US 2012/0077282 A1 Mar. 29, 2012

Related U.S. Application Data

(63) Continuation-in-part of application No. 11/351,181, filed on Feb. 8, 2006, now Pat. No. 8,119,066.

(51) Int. Cl.
*G01N 21/00* (2006.01)
*G01J 3/02* (2006.01)
(Continued)

(52) U.S. Cl.
CPC ............... *G01J 3/02* (2013.01); *G01J 3/0202* (2013.01); *G01J 3/021* (2013.01); *G01J 3/0218* (2013.01); *G01J 3/0232* (2013.01); *G01J 3/0235* (2013.01); *G01J 3/0256* (2013.01); *G01J 3/0291* (2013.01); *G01J 3/10* (2013.01); *G01J 3/427* (2013.01); *G01J 3/4406* (2013.01); *G01N 21/6408* (2013.01); *G01N 21/6428* (2013.01); *G01N 21/6445* (2013.01); *G01N 21/645* (2013.01); *G01N 21/763* (2013.01); *G01N 2021/1738* (2013.01); *G01N 2021/6415* (2013.01); *G01N 2021/6419* (2013.01); *G01N 2021/6441* (2013.01); *G01N 2021/6482* (2013.01);
(Continued)

(58) Field of Classification Search
None
See application file for complete search history.

(56) References Cited

U.S. PATENT DOCUMENTS 3,806,259 A 4/1974 Boostrom et al.
6,200,531 B1 3/2001 Liljestrand et al.
(Continued)

FOREIGN PATENT DOCUMENTS

DE 4327752 2/1995
EP 1279946 7/2001
(Continued)

OTHER PUBLICATIONS

Office Action for CN 2007800047561, mailed Mar. 16, 2010.

*Primary Examiner* — Robert Xu
(74) *Attorney, Agent, or Firm* — Bella Fishman

(57) ABSTRACT

A cartridge and cartridge system for use in an apparatus for analyzing a sample are provided. The system has a plurality of cartridges for different applications for a multimode instrument. The cartridges are removably engaged with a cartridge support of the apparatus in a "plug-in" format such that one cartridge may be removed from the apparatus and another cartridge may be easily installed. The cartridge support includes a plurality of cartridge positions that receive cartridges concurrently. One of the cartridges may be a luminescence cartridge that includes an integrated detector that is movable toward and away from a sample carrier of the apparatus, and thus toward and away from a sample located at the sample carrier.

28 Claims, 23 Drawing Sheets

(51) Int. Cl.
- *G01J 3/10* (2006.01)
- *G01J 3/427* (2006.01)
- *G01J 3/44* (2006.01)
- *G01N 21/76* (2006.01)
- *G01N 21/64* (2006.01)
- *G01N 21/17* (2006.01)

(52) U.S. Cl.
CPC .. *G01N2201/024* (2013.01); *G01N 2201/0618* (2013.01); *G01N 2201/062* (2013.01); *G01N 2201/0621* (2013.01); *G01N 2201/0692* (2013.01); *G01N 2201/0696* (2013.01)
USPC .......................................... 422/67; 436/172

(56) References Cited

U.S. PATENT DOCUMENTS

| | | | |
|---|---|---|---|
| 6,310,687 | B1 | 10/2001 | Stumbo et al. |
| 6,379,969 | B1 | 4/2002 | Mauze et al. |
| 6,409,909 | B1 | 6/2002 | Spichiger-Keller et al. |
| 6,517,777 | B2 | 2/2003 | Liljestrand et al. |
| 6,580,081 | B1 | 6/2003 | Thorwirth |
| 6,795,189 | B2 | 9/2004 | Booker et al. |
| 6,822,741 | B2 | 11/2004 | Aronkyto et al. |
| 6,878,947 | B2 | 4/2005 | Haberstroh |
| 6,891,618 | B2 | 5/2005 | Harju et al. |
| 7,670,848 | B2 | 3/2010 | Gambini et al. |
| 2002/0043626 | A1 | 4/2002 | Booker et al. |
| 2002/0060791 | A1 | 5/2002 | Stumbo et al. |
| 2002/0113213 | A1 | 8/2002 | Amirkhanian et al. |
| 2003/0042428 | A1 | 3/2003 | Peukert et al. |
| 2003/0048445 | A1 | 3/2003 | Tokhtuev et al. |
| 2003/0048446 | A1 | 3/2003 | Aronkyto et al. |
| 2003/0048447 | A1 | 3/2003 | Harju et al. |
| 2003/0117628 | A1 | 6/2003 | Harju et al. |
| 2003/0118477 | A1 | 6/2003 | Liljestrand et al. |
| 2004/0057870 | A1 | 3/2004 | Isaksson et al. |
| 2004/0120857 | A1 | 6/2004 | Smith et al. |
| 2005/0012252 | A1 | 1/2005 | Yu et al. |
| 2005/0012929 | A1 | 1/2005 | Booker et al. |
| 2005/0023445 | A1 | 2/2005 | Horn et al. |
| 2005/0062969 | A1 | 3/2005 | Harju et al. |
| 2005/0063279 | A1 | 3/2005 | Song et al. |
| 2005/0105080 | A1 | 5/2005 | Landlinger |
| 2005/0109950 | A1 | 5/2005 | King |
| 2005/0201441 | A1 | 9/2005 | Seyfried et al. |

FOREIGN PATENT DOCUMENTS

| | | |
|---|---|---|
| JP | 2003-195177 | 7/2003 |
| JP | 2005-345717 | 12/2005 |

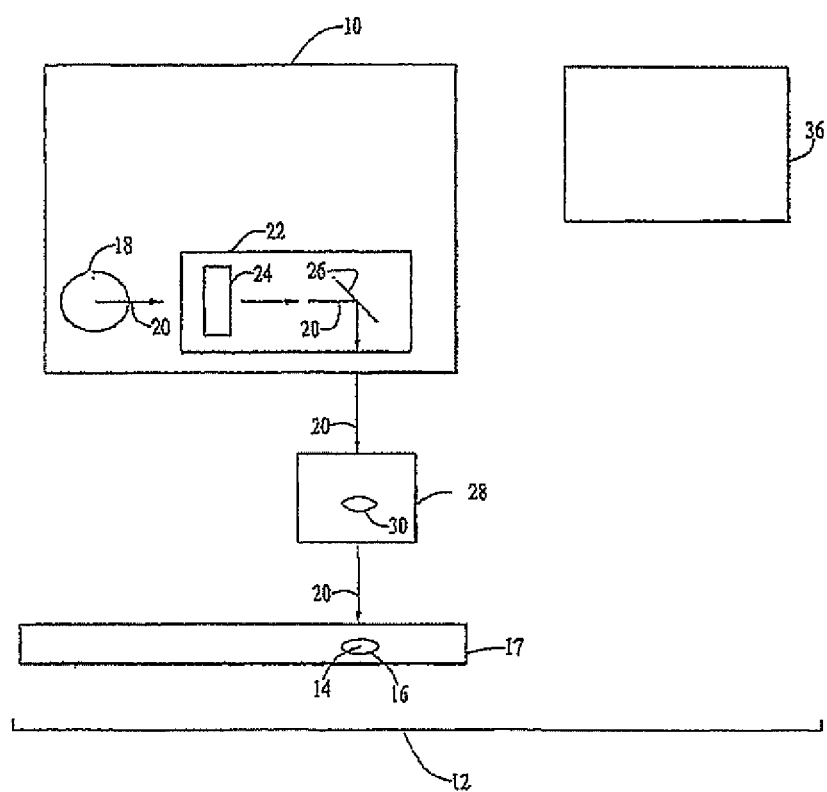

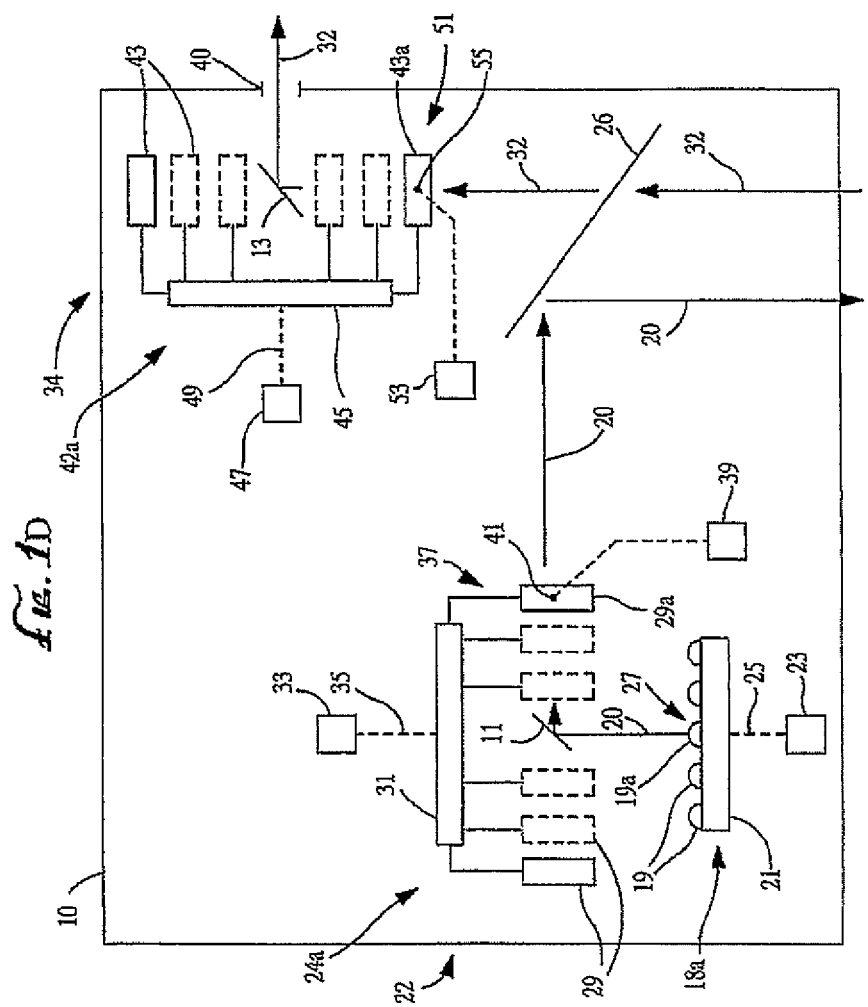

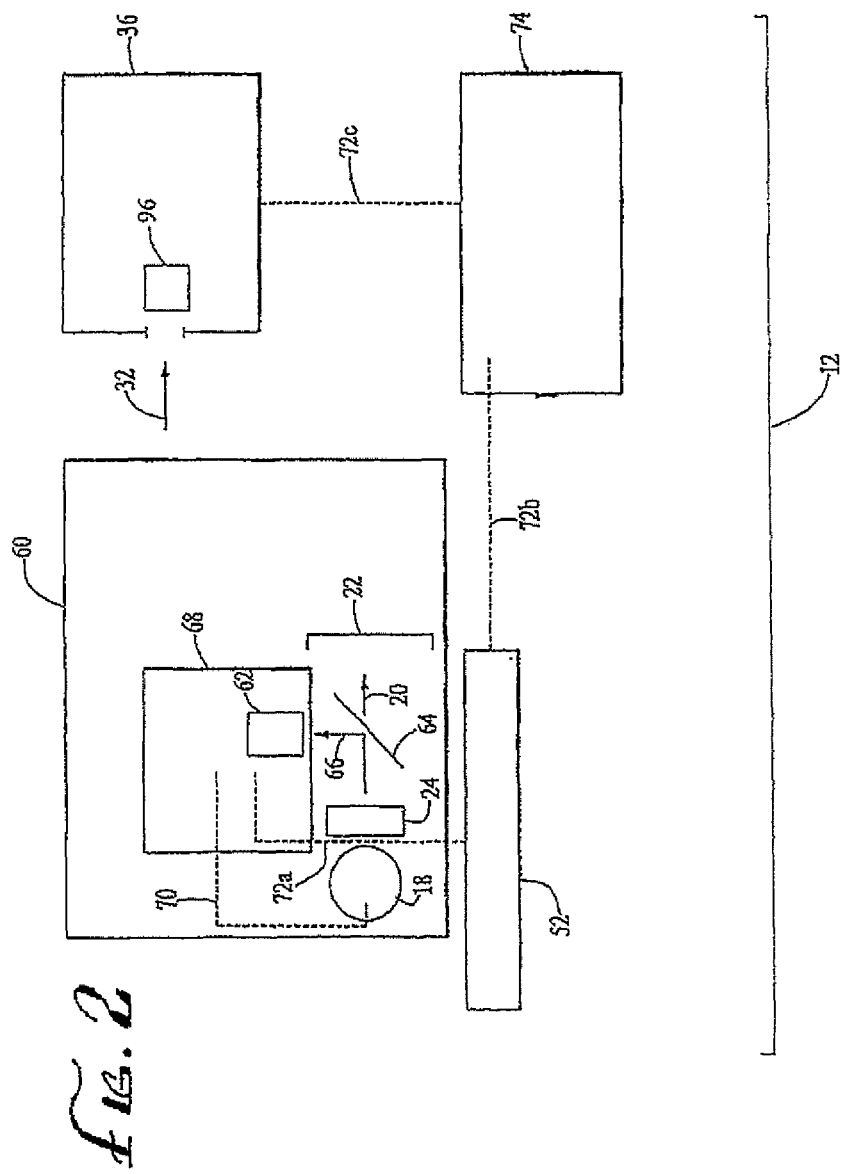

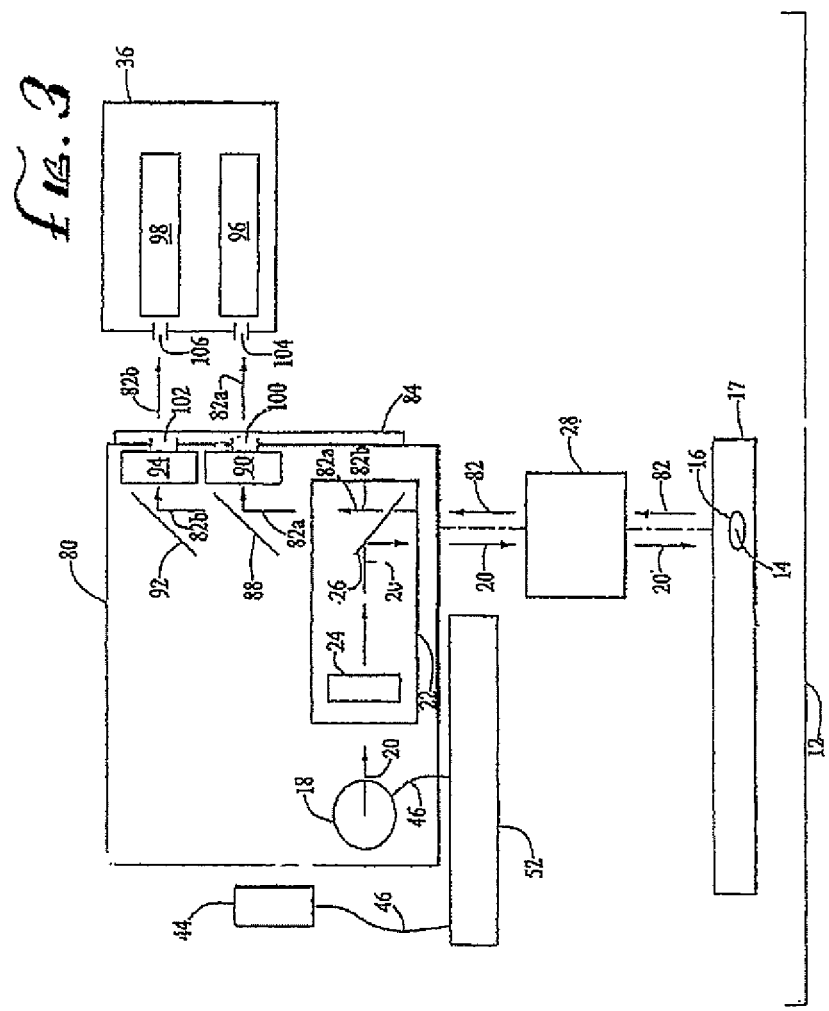

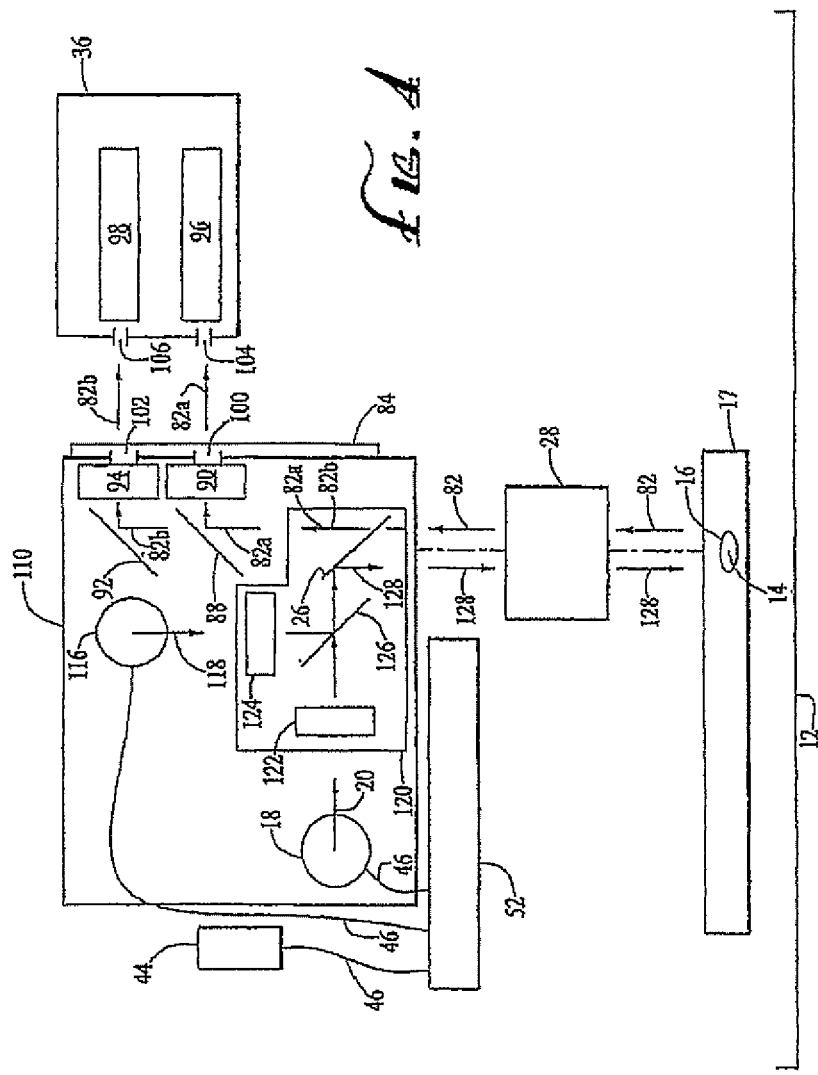

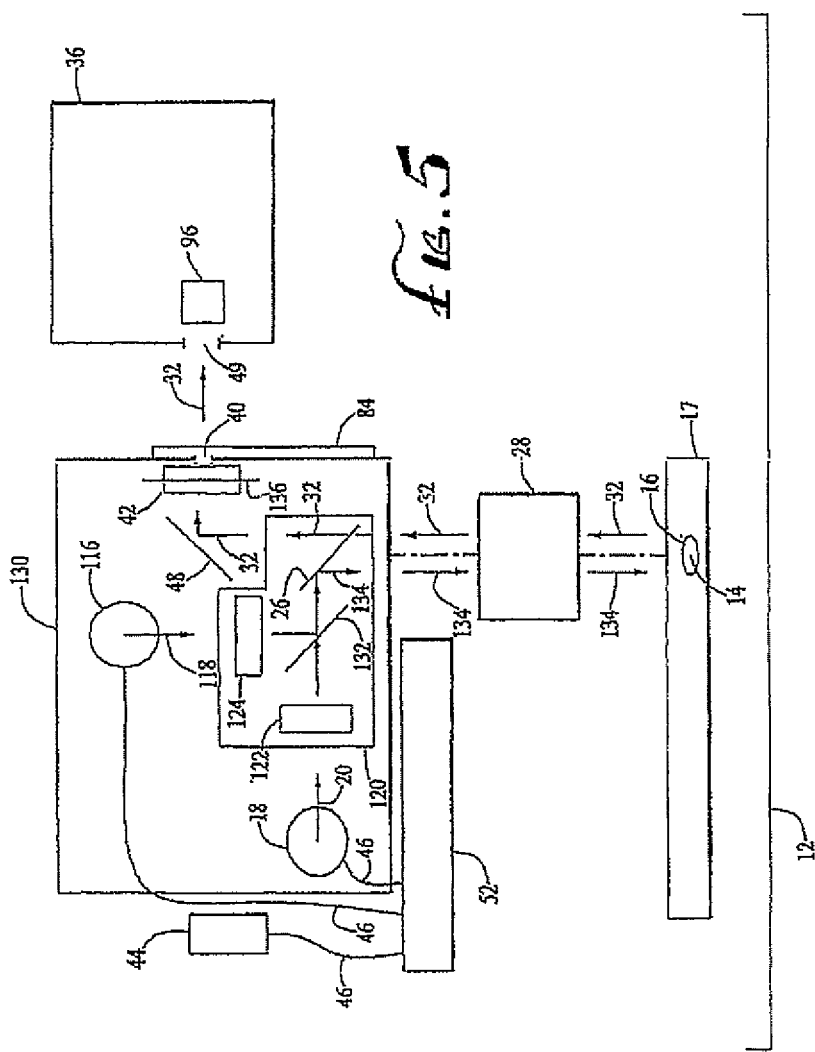

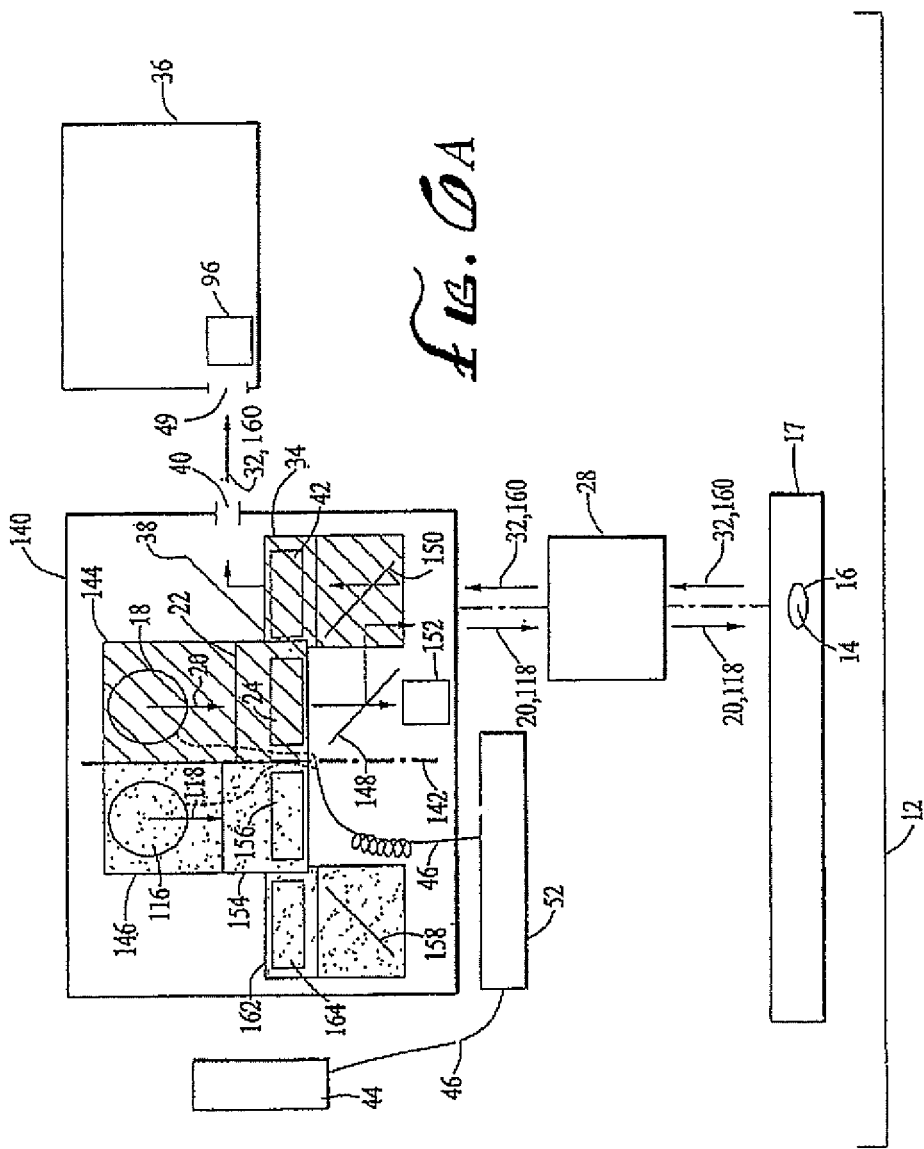

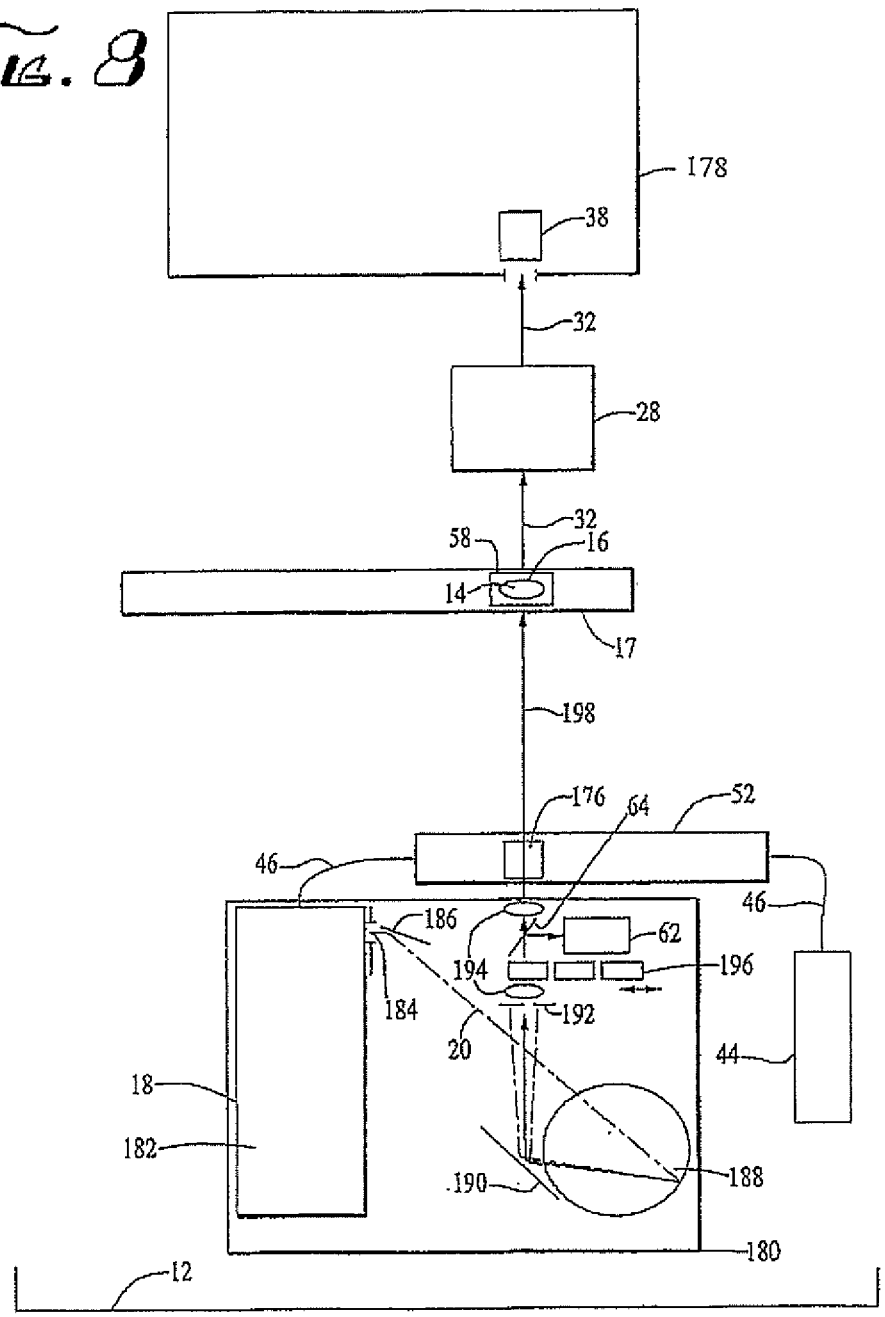

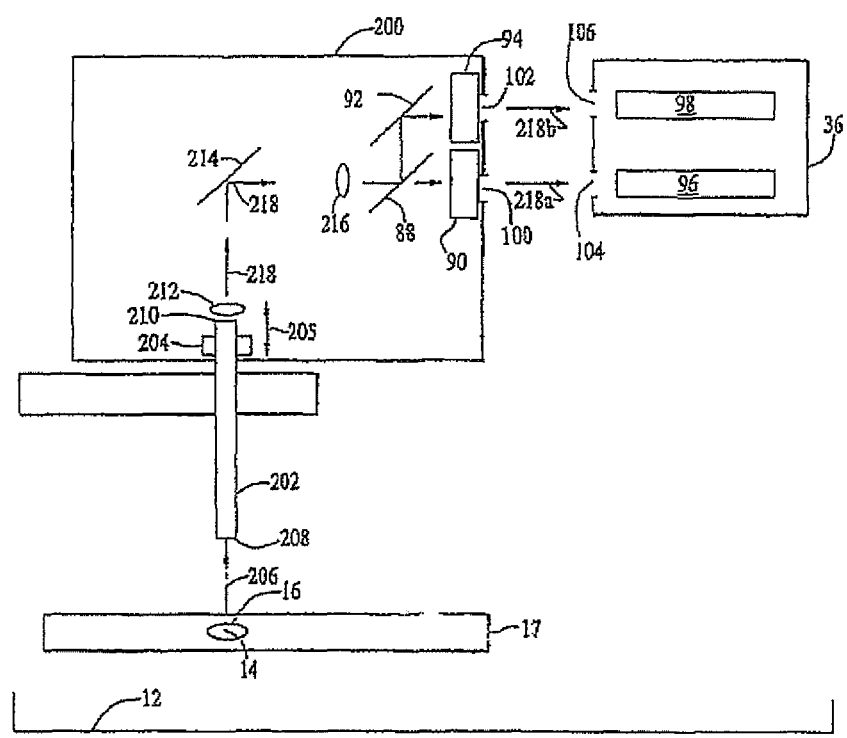

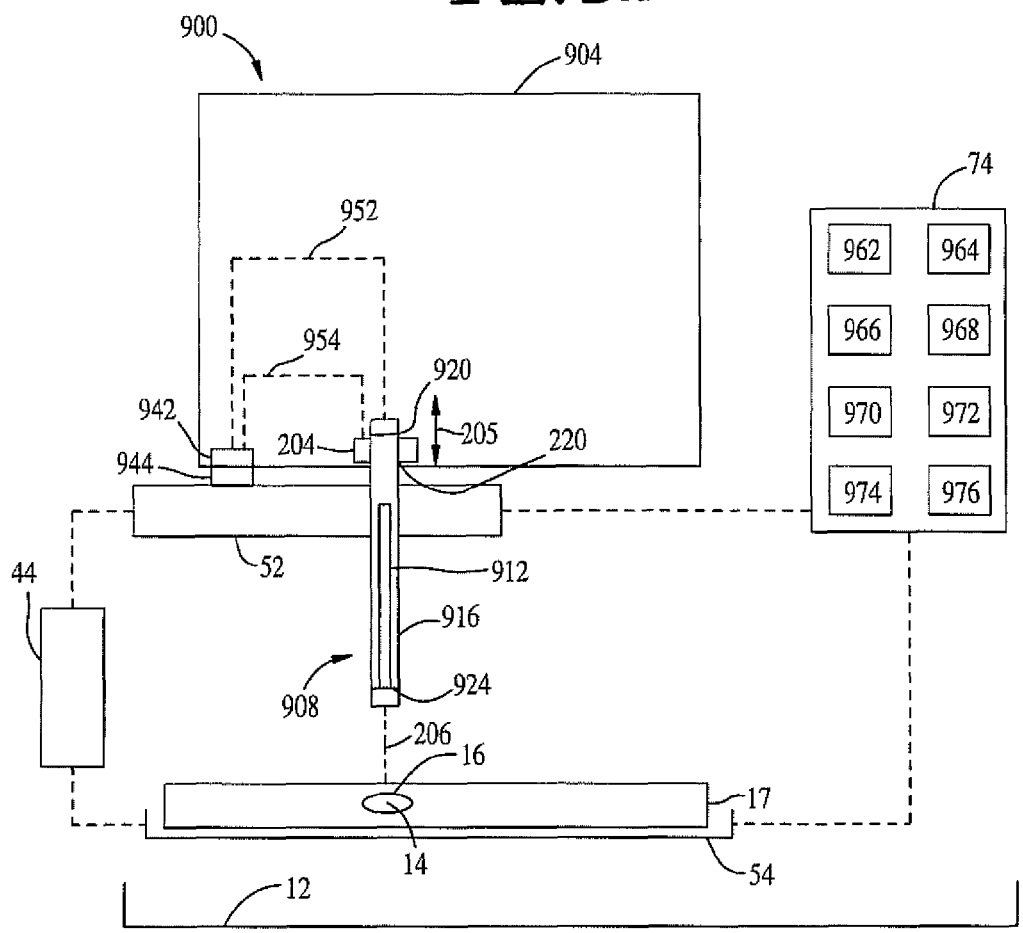

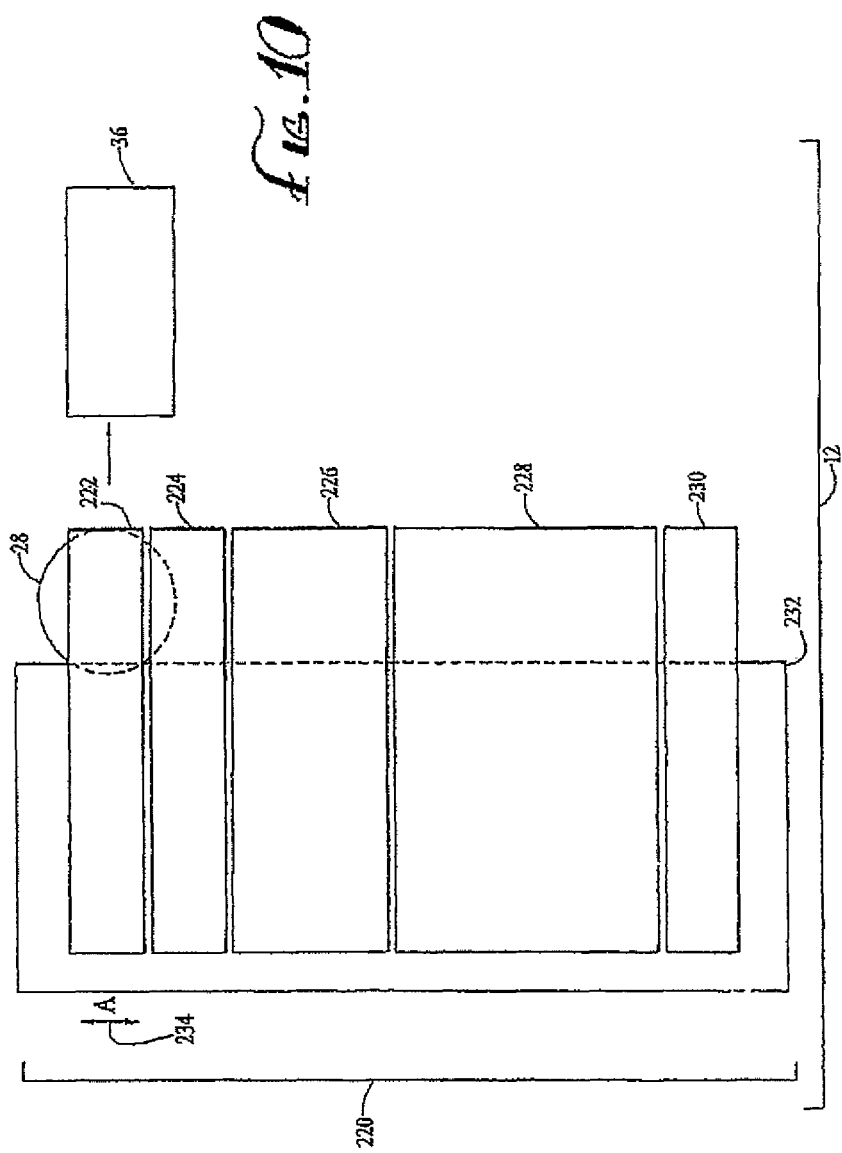

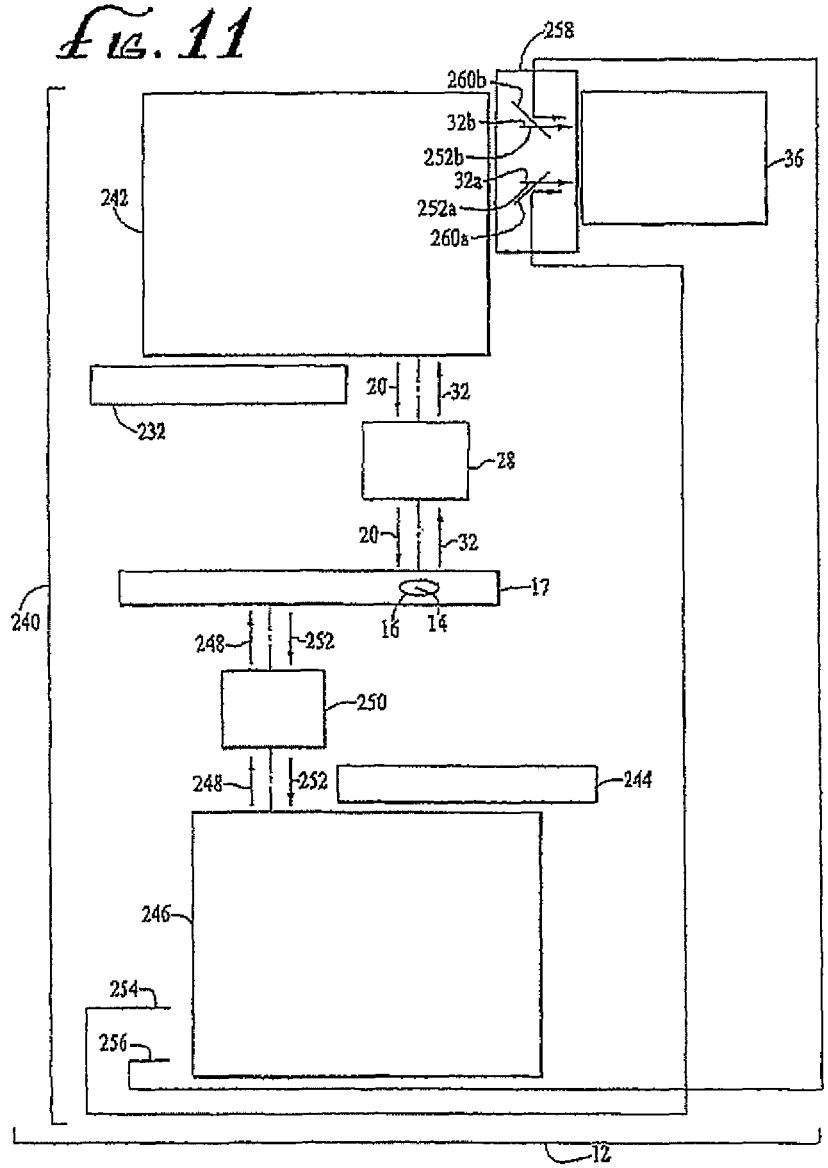

LUMINESCENCE MEASUREMENT UTILIZING CARTRIDGE WITH INTEGRATED DETECTOR

RELATED APPLICATIONS

This application is a continuation-in-part of co-pending U.S. patent application Ser. No. 11/351,181, filed on Feb. 8, 2006, and titled "MULTIMODE READER," the content of which is incorporated by reference herein in its entirety.

TECHNICAL FIELD

This present invention generally relates to multimode analytical instruments, cartridges utilized with such instruments, and methods related to such instruments and cartridges. In particular, the invention relates to measuring luminescent emissions from samples utilizing such instruments, cartridges and methods.

BACKGROUND

Multimode analytical instruments, also referred to as multimode readers, are apparatus that can perform multiple analytical assays in a single instrument. Standard multimode readers, used within the life science industry, can measure the most common types of assays (i.e., applications, such as fluorescence, luminescence, and absorbance) in a single instrument. The use of a single instrument to perform these assays is advantageous over using multiple dedicated instruments to perform the same measurements. This lies in the fact that a multimode reader can provide ease of use, a better price performance ratio, and require less bench top area than multiple instruments.

Multimode readers having a certain level of modularity are known. Further information on these instruments can be found in US Patent Application Nos. 2005/0012929; 2005/0105080; and US 2003/0048447, for example.

Generally, these instruments have built-in general purpose (i.e., white) light sources, such as halogen lamps and xenon flash lamps, and general purpose detectors such as photomultiplier tubes (PMTs) and silicon photodiodes. Also, in these instruments, optical filters have been mounted into wheels or slides, and application specific beamsplitters have been installed into slides, or into revolver like mechanisms.

However, with the above described instrumentation, performing a specific application means, from the hardware point of view, accessing a multitude of driven stages, at runtime, for selecting the correct combination and adjustment of filters, beamsplitters, apertures, and lightguides, for example. In these devices, enabling new applications of a given technology requires retrofitting specific optical filters and beamsplitters. Further, new configurations demand the correct definition for the new filters within the instrument control software.

Moreover, a multimode reader should ideally be capable of implementing a multitude of different applications and detection techniques and be expected to come close to the performance of dedicated instruments, while minimizing costs without excessively making comprises to any detection modality.

Therefore, there is a need for an improved and more efficient multimode reader instrument. There is also a need for a multimode reader instrument that can change applications and have the identification of the programmed parameters for the new application be performed automatically. There is also a need for a multimode reader instrument that can be easily upgraded for new types of applications. There is also a need for a multimode reader instrument capable of implementing detection techniques at an enhanced level of performance that approaches the level of performance of dedicated instruments. As one example there is a need for a multimode reader instrument capable of implementing luminescence detection techniques at an enhanced level of performance approaching that afforded by dedicated luminometers.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a system for analyzing a target in a sample includes an apparatus housing; a power source disposed in the apparatus housing; a sample carrier disposed in the apparatus housing; a cartridge support disposed in the apparatus housing and comprising a plurality of cartridge positions configured for receiving a plurality of removable cartridges concurrently; and a luminescence cartridge removably mounted at one of the cartridge positions. The luminescence cartridge includes a cartridge housing having an opening; a driver disposed in the cartridge housing and communicating with the power source; and a luminescence detector communicating with the power source and coupled to the driver, wherein the luminescence detector is movable by the driver through the opening and alternately toward and away from the sample carrier.

In some embodiments, the luminescence detector includes a photomultiplier tube or a photodiode. In some embodiments, the luminescence detector is configured for single photon counting.

In some embodiments, the cartridge support is movable into and out from the apparatus housing.

In some embodiments, the sample carrier is configured for carrying a sample support configured for supporting a plurality of samples, and the sample carrier is configured for sequentially moving one or more selected samples into alignment with the luminescence detector.

In some embodiments, an optical detector is disposed in the apparatus housing at a location external to the luminescence cartridge, wherein the cartridge support is movable in the apparatus housing and configured for selectively aligning one or more removable cartridges mounted at one or more respective cartridge positions with the optical detector.

In some embodiments, a read head is disposed in the apparatus housing external to the luminescence cartridge, wherein the cartridge support is movable in the housing and configured for selectively aligning one or more removable cartridges mounted at one or more respective cartridge positions with the read head.

In some embodiments, the sample carrier is configured for carrying a sample support configured for supporting a plurality of samples, and the sample carrier is configured for sequentially moving one or more selected samples into alignment with the read head.

In some embodiments, one or more additional cartridges are removably mounted at one or more respective cartridge positions concurrently with the luminescence cartridge. The additional cartridges may be, for example, fluorescence cartridges, absorbance cartridges, and/or injector cartridges. An injector cartridge may include a reagent reservoir, a pump, and a nozzle movable toward the sample carrier from within the injector cartridge.

According to another embodiment, a method for analyzing a target in a sample includes loading a luminescence cartridge on a cartridge support of an apparatus to position the luminescence cartridge in an apparatus housing; moving a sample carrier disposed in the apparatus housing and supporting the sample, to align the sample with a luminescence detector of the luminescence cartridge; moving the luminescence detector toward the sample until the luminescence detector has reached a desired distance to the sample; and receiving luminescent light emitted from the sample at the luminescence detector.

In some embodiments, loading includes opening a panel of the apparatus to access the cartridge support.

In some embodiments, before loading the luminescence cartridge, a previously loaded cartridge is removed from the cartridge support, wherein loading the luminescence cartridge replaces the previously loaded cartridge with the luminescence cartridge.

In some embodiments, an additional cartridge is loaded at another cartridge position, wherein the luminescence cartridge and the additional cartridge are loaded on the cartridge support concurrently. In some embodiments, the cartridge support is moved in the apparatus housing until the additional cartridge is aligned with an optical detector disposed in the apparatus housing at a location external to the luminescence cartridge.

In some embodiments, an iris of the luminescence detector is adjusted to adjust a numerical aperture of the luminescence detector. In some embodiments, adjusting the iris includes providing power to the iris from a power source, transmitting a control signal to the iris from a system controller of the apparatus, or both.

In some embodiments, the luminescent detector may be retracted completely into the luminescence cartridge.

In some embodiments, a measurement signal is transmitted from the luminescence detector to signal processing circuitry of the apparatus.

In some embodiments, a glow luminescence reagent or a flash luminescence reagent is added to the sample before receiving the luminescent light.

According to another embodiment, a luminescence cartridge for use in an apparatus for analyzing a target in a sample includes a cartridge housing having an opening; a driver disposed in the cartridge housing; a luminescence detector at least partially disposed in the cartridge housing and coupled to the driver, wherein the luminescence detector is movable by the driver through the opening and alternately toward and away from the cartridge housing; and an electrical connector mounted at the cartridge housing and in signal communication with the driver and the luminescence detector, the electrical connector configured for removable coupling to the apparatus to receive power from and transmit signals to the apparatus.

In some embodiments, the luminescence detector includes an iris configured for adjusting a numerical aperture of the luminescence detector.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 2 is a schematic view of an example of a cartridge having source intensity monitoring components according to an embodiment of the present invention.

FIG. 5 is a schematic view of an example of a dual excitation cartridge according to an embodiment of the present invention.

FIGS. 6A and 6B are schematic views of an example of a multi-purpose cartridge, having multiple applications mounted on a revolver mechanism within the cartridge, according to an embodiment of the present invention.

FIG. 8 is a schematic view of an example of a wide band light source cartridge with wavelength selection according to an embodiment of the present invention.

FIG. 9 is a schematic view of an example of a luminescence cartridge, having an integrated read head, according to an embodiment of the present invention.

FIG. 9A is a schematic view of an example of a luminescence cartridge, having an integrated detector, according to another embodiment of the present invention.

FIG. 10 is a schematic top view of an example of a cartridge system according to an embodiment of the present invention.

FIG. 11 is a schematic view of an example of a top and bottom reading cartridge system according to an embodiment of the present invention.

DETAILED DESCRIPTION

According to the present invention, a cartridge for use in an apparatus for analyzing a sample is provided. The cartridge has one or more light sources, as well as optical systems and other components, which are specific for a certain type of application such as fluorescence or absorbance. The light source, optical systems, and other components for a specific application are housed in a single cartridge. The cartridge is removably engaged with the apparatus in a "plug-in" format such that the apparatus can be upgraded by substitution or installation of a cartridge, i.e., a new application can be installed by adding or substituting a new cartridge in the apparatus, or an installed cartridge can be substituted with another cartridge of the same purpose which incorporates the latest advancements in technology. The new cartridge may have its components preadjusted and pretested and the cartridge may be automatically identifiable by the apparatus such that the instrument control software can identify an individual cartridge and recognize any application specific parameters stored in the cartridge. Thus, instead of selecting a combination of light sources, optics, and other components for a new application, running a new application is reduced to selecting a single component, i.e., the cartridge, with its interior components preadjusted and pretested, and installing the cartridge in the apparatus. An advantage of the cartridge concept is that an instrument can be upgraded in the field by the user himself—without needing the assistance of a service engineer.

The apparatus may have general purpose detectors (like photomultipliers and photodiodes), which are shared by multiple cartridges, and all applications of the same technology may share certain read heads that interface with the samples to be measured.

Also provided is a luminescence cartridge that includes an integrated detector, and which thus does not require the use of the general purpose detector provided with the apparatus.

Figure 1B:
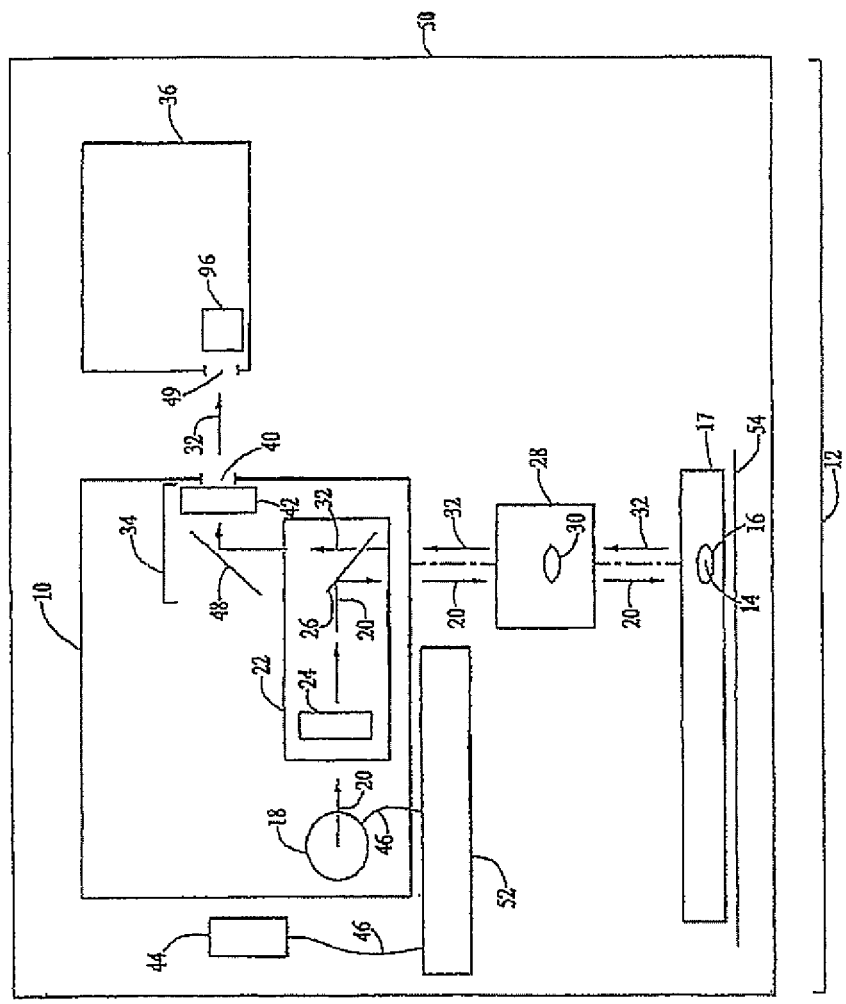
FIG. 1B is a schematic view of an example of components of a cartridge used for a fluorescence application according to an embodiment of the present invention.
Figure 1C:
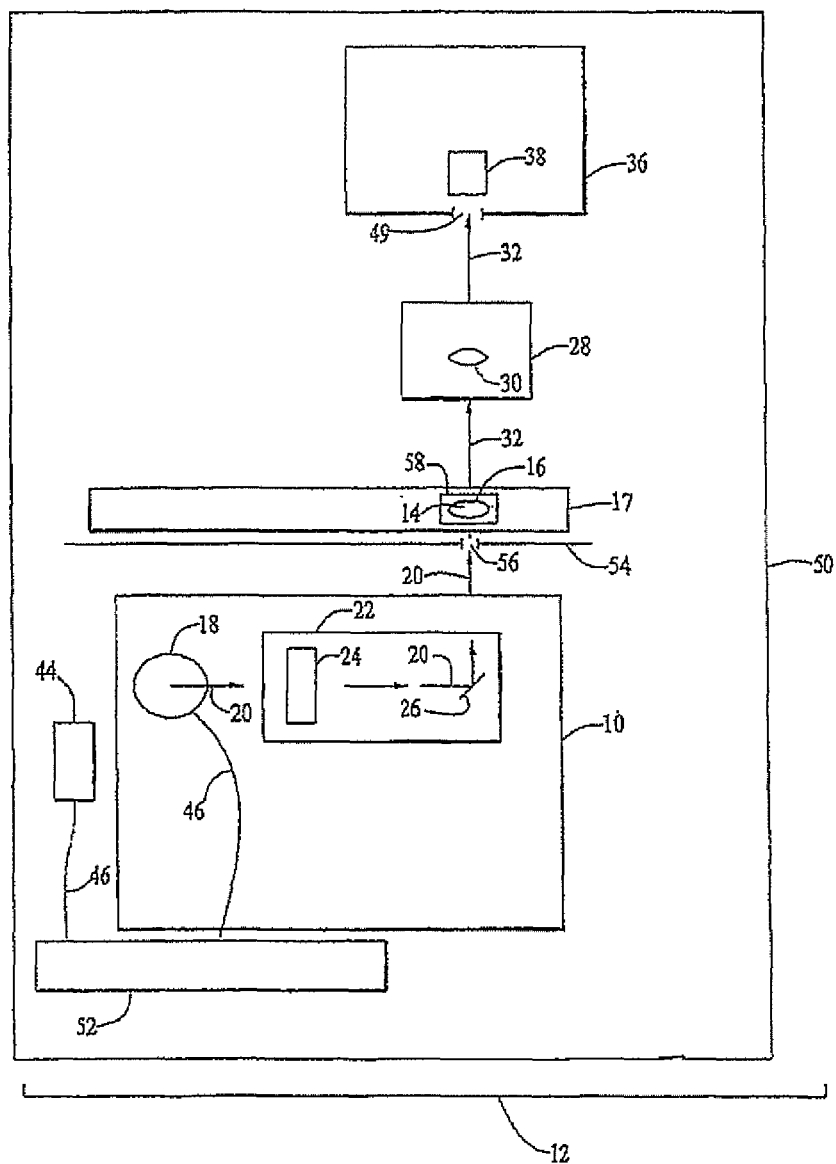
FIG. 1C is a schematic view of an example of components of a cartridge used for an absorbance application according to an embodiment of the present invention.
Figure 1E:
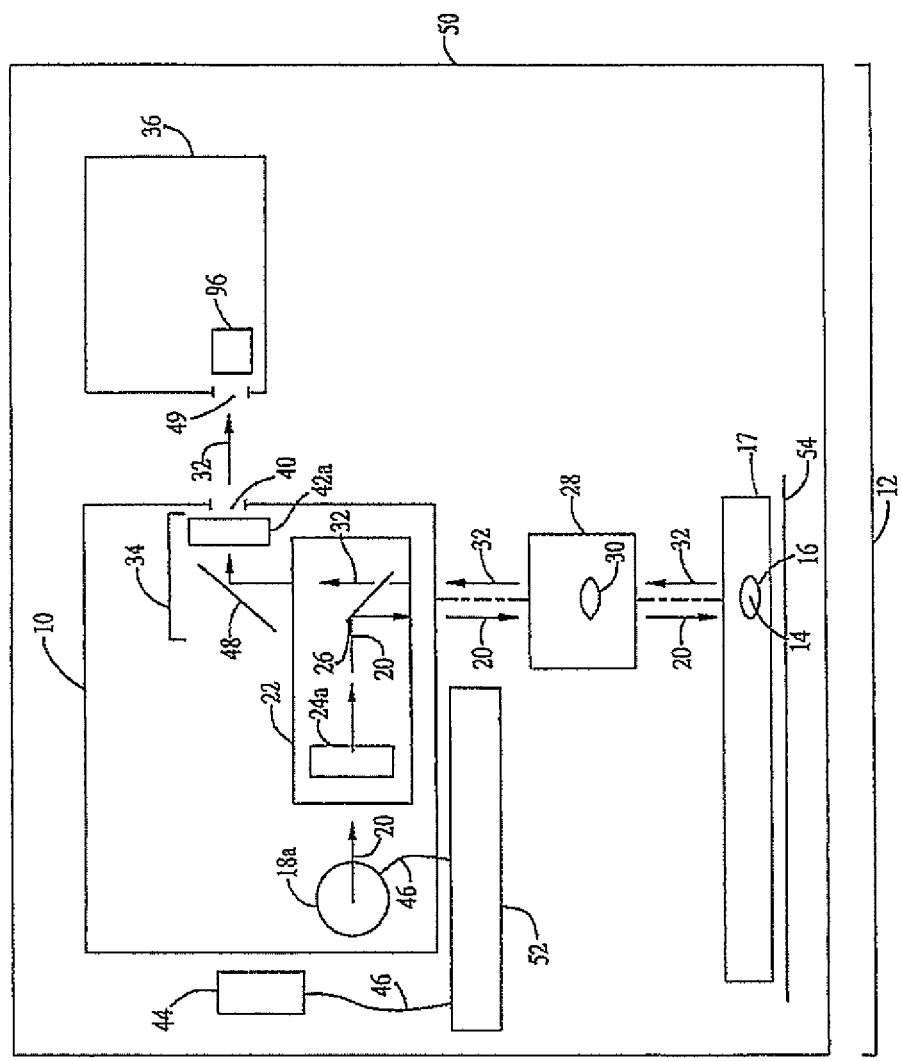
FIG. 1A is a schematic view of an example of components of a cartridge according to an embodiment of the present invention.

Referring now to FIGS. 1A, 1B, and 1C a cartridge 10 for use in an apparatus 12 for analyzing a target 14 in a sample 16 is shown. The sample 16 may be held within the apparatus 12 on a sample support 17, such as a microplate. As shown in FIG. 1, the cartridge 10 comprises one or more light sources 18 that separately or in combination produce an exciting light 20. The cartridge 10 is designed to be removably engaged with the apparatus 12. The cartridge 10 has a first optical system 22 which has components for directing the exciting light 20 to the sample 16. The light source 18, such as a light emitting diode (LED) or a laser diode (LD), is collimated by lenses and apertures to emit a collimated beam of light. The first optical system 22 then transmits the exciting light 20 through filters 24, such as a bandpass filter, and then reflects the exciting light 20 out of the cartridge 10 with the help of a reflector 26, such as a dichroic beamsplitter, to a read head 28. The read head 28 directs the exciting light 20 toward the sample 16. The read head 28 contains an objective lens 30 that can be moved up and down. The objective lens 30 focuses the exciting light 20 onto the sample 16. The sample 16, containing the target 14, then produces an emitting light 32 (or emitted light 32), which is directed to an optical output detector 36, having a photomultiplier tube (PMT) 96, as shown in FIG. 1B, or a photodiode 38, as shown in FIG. 1C.

As also shown in FIGS. 1B and 1C the apparatus 12 is part of a system for analyzing a sample. The system comprises a structure 50, also referred to herein as a housing or apparatus housing, which is engaged (i.e., attached) to the read head 28, the detector 36, a power source 44, and a movable cartridge support 52. The movable cartridge support 52 positions the cartridge 10 within the apparatus 12 and is capable of supporting a plurality of cartridges and aligning each cartridge with the read head 28 and the detector 36. The cartridge 10 has a coupler 46 for providing a current supply from the power source 44 to the light source 18. Preferably, the cartridge 10 is mounted onto the support 52 and a plug terminating the electronics inside of the cartridge 10 is connected with a socket in the support 52. At the socket, several low voltage output lines of the power source 44 are available and interface lines with the main apparatus controller. The coupler 46 functions in connecting the cartridge 10 with other components in the apparatus 12, such as for receiving low DC voltage for the cartridge light source 18 and other electronics; establishing control lines for LED current adjustment; establishing control lines for cartridge recognition; data lines (e.g., an electronic bus) for detectors within the cartridge 10 (e.g., a photodiode for sending measured data to a controller); and synchronization lines for synchronizing pulses of the light source 18 with the data acquisition from detector(s) and other circuitry within the apparatus 12, such as photon counting circuitry in the main apparatus controller. Preferably, the coupler 46 is made from two parts, a printed circuit board that extends along the cartridge support 52, providing a socket for one or more cartridges 10, and a flexible flat cable at the end, bridging the gap to the main apparatus controller (flexible, because the cartridge support 52 can be moved). The electronic bus, or data line function is designed as of the type SPI (serial peripheral interface).

The system may also have a sample support carrier (or sample carrier) 54, such as a microplate scanning stage, attached to the structure for moving the sample support 17 either horizontally or vertically within the apparatus housing (e.g., structure 50).

Referring now to FIG. 1B, in certain embodiments, such as a cartridge 10 that is used for a fluorescence application, the emitting light 32 is collected from the target 14 by the read head 28 and collimated back into the cartridge 10. The cartridge 10 has a second optical system 34, which receives the emitted light 32 from the read head 28 and directs the emitted light 32 from the sample 16 to the detector 36. The emitting light 32 received from the read head 28 is transmitted through the reflector 26, and is then directed with a reflector 48 towards the cartridge exit 40, which interfaces with the detector 36 via a detector port 49. Before exiting the cartridge 10, the emitted light 32 is filtered through a filter 42, such as a bandpass filter, to reject contributions of excitation light being scattered back from the read head 28 and the sample 16. The entire path after the emitted light 32 has passed through the reflector 26 is optically shielded from those areas of the cartridge 10 which may be floated with diffuse scatter of exciting light 20.

Referring now to FIG. 1C, in certain embodiments, a cartridge 10, such as a cartridge that is used for an absorbance application, is positioned in the apparatus 12 in opposite to the detector 36. According to this embodiment, the exciting light 20 is transmitted through the sample 16 and sample support carrier 54 via an aperture 56 (i.e., a window or light transparent portion) in the sample support carrier 54 and an aperture 58 (i.e., a window or light transparent portion) in the sample support 17. Emitting light 32 from the target 14 is directed to the detector 36 (containing, e.g., a photodiode 38). The configuration of the cartridge 10 for measuring absorbance as shown in FIG. 1C is shown by way of example and other configurations are possible, for example, the cartridge 10 may be alternately positioned within the apparatus 12, such as in the same approximate plane as the detector 36 (e.g., side-by-side), and the emitting light 32 may be relayed to the detector 36, such as with a light guide, as will be understood by those of skill in the art with reference to this disclosure.

The one or more light sources 18 housed in the cartridge 10 may be selected from suitable light sources known to those of skill in the art such as light emitting diodes (LEDs), laser-diodes, and a Xenon flash lamp module. Preferably, when the cartridge 10 is used for a fluorescence application, such as shown in FIG. 1B, the light source 18 is one or more LED light sources. Preferred LED light sources are obtained from Lumileds, San Jose, Calif., US (for various peak wavelengths between 350 nm and 700 nm; Luxeon Star, Nichia, Tokushima, Japan, for various peak wavelengths between 350 nm and 700 nm; and Roithner-Laser, Vienna, Austria, for various peak wavelengths between 350 nm and 700 nm. Preferably, when the cartridge 10 is used for an absorbance application, such as shown in FIG. 1C, the light source 18 is a Xenon flash lamp module. Preferred Xenon flash lamp modules are obtained from Perkin Elmer Optoelectronics, Fremont, Calif., US, product name RSL3100; and Hamamatsu Photonics, Japan, product name L9455.

Referring now to FIG. 2, another embodiment of the apparatus 12 for analyzing a target 14 in a sample 16 is shown. According to this embodiment, the apparatus 12 has a source intensity monitoring cartridge 60 with a light source 18 and a first optical system 22 which has components for directing an exciting light beam 20 to a sample 16 via a read head, as described with respect to FIG. 1B. The cartridge 60 is designed to be removably engaged with apparatus 12 via the movable cartridge support 52. In certain embodiments, the cartridge 60 has a second optical system 34 (not shown), as described with respect to FIG. 1B, which receives emitting light 32 from the sample 16 via the read head (not shown) and directs the emitting light 32 from the sample 16 to the detector 36.

According to the embodiment shown in FIG. 2, during or prior to signal detection at the detector 36, the exciting light beam 20 is passed through an excitation filter 24 and a portion of the exciting light beam 20 is reflected onto a light source detector 62 (e.g., a photodiode) with a partially reflecting mirror 64 as reflected light 66. Electronic circuitry 68 measures the intensity level of the reflected light 66. The measured intensity level of the reflected light 66 is used to stabilize the output of the light source 18 via a feedback loop 70.

In another embodiment shown in FIG. 2, when analyzing a target 14 in a sample 16 with the detector 36 using a fluorescence method, as described with respect to FIG. 1B, the electronic path 72a, 72b, and 72c may be applied to extend the generic dynamic range of the detector 36. According to this embodiment, the light source 18 is first adjusted to a maximum intensity, and the intensity of the emitting light 32 is tested (for quite a short pre read time to give a pre read value) at the detector 36. The main controller 74 receives the tested emitting light signal from the detector 36 via path 72c and may adjust the intensity of the exciting light 20 (i.e., the source intensity) by addressing the controller 68 via control line 72a and 72b. Preferably, when detecting a superthreshold signal at detector 36, the main controller 74 reduces the intensity of the exciting light 20 by adjusting the power to light source 18 according to the pre read value. In this preferred embodiment, the target 14 is measured with a longer read time, as selected by the user, and the intensity of the signal from the emitting light 32 found at the detector 36 is normalized with the actual value of the intensity of the exciting light 20, because the intensity of the emitting light 32 changes according to the intensity of the exciting light 20. Thus, the read out becomes comparable with measurement values taken at other light source intensity levels.

In fluorescence applications, the LED light source(s) are typically supplied with constant current for reading of prompt fluorescence, where prompt fluorescence is differentiated from time delayed fluorescence reading, e.g., in prompt fluorescence, the fluorescence emission is instantaneously gone when the light source is switched off—unless operating on nanosecond time scales (fluorescence labels having typical decay times of about 1 to about 10 nanoseconds). In other fluorescence applications using a light source 18 that can be pulsed (e.g., LEDs, laser diodes, and Xenon flash lamps), enables the measurement of fluorescence with a time delay (i.e., "time-resolved," in connection with lanthanide ion labels having decay times between about 20 and about 2,000 microseconds). In such applications, the photon counting electronics, (to be thought as included in the detector 36) monitoring the sample emission are enabled (gated by the controller 74 via control line 72c) with a short time delay after the light source 18 has been switched off by controller 74 via control line 72a and 72b.

Figure 3A:
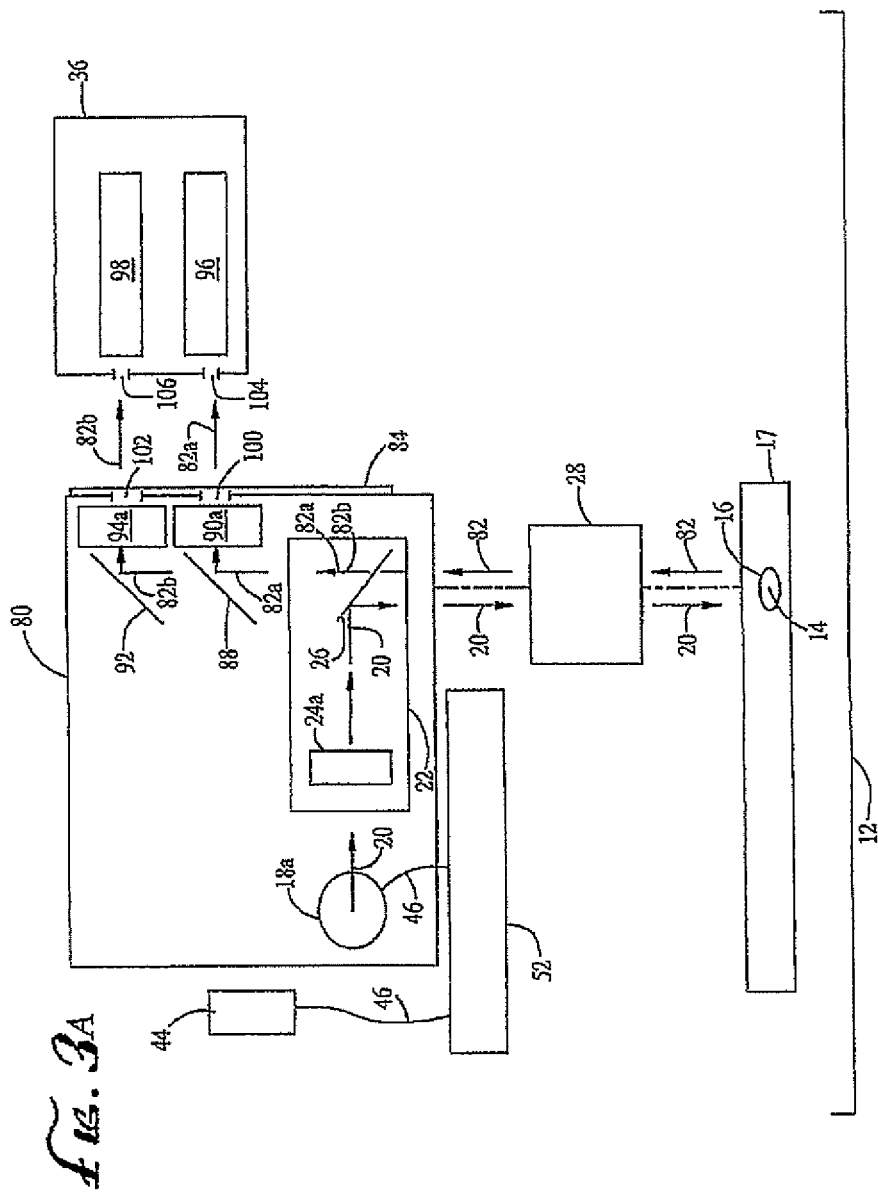
FIG. 3 is a schematic view of an example of a dual emission cartridge according to an embodiment of the present invention.

Referring now to FIG. 3, another embodiment of the apparatus 12 for analyzing a target 14 in a sample 16 is shown. According to the embodiment shown in FIG. 3, the apparatus 12 has a dual emission cartridge 80 that is capable of measuring dual label assays. The dual emission cartridge 80 is designed to be removably engaged with apparatus 12 via the movable cartridge support 52. Certain assays profit from measuring two different emission wavelengths at the same time (e.g., Fluorescence Resonance Energy Transfer (FRET) type assays), and measuring two different emission wavelengths at substantially the same time can result in a total time saving for the user due to the reduced read time.

According to the embodiment shown in FIG. 3, the apparatus 12 has a light source 18 which produces an exciting light 20, such as described with respect to FIG. 1B. The apparatus 12 additionally has a power source 44 and the cartridge 80 has a coupler 46 for providing a current supply to the light source 18 from the power source 44. The dual emission cartridge 80 has a first optical system 22 which has components, including an excitation filter 24, for directing the exciting light 20 to a sample 16 via a read head 28. The read head 28 directs the exciting light 20 toward the sample 16. The sample 16, containing the target 14, produces an emitting light 82. The dual emission cartridge 80 has a second optical system 84, which receives the emitting light 82 from the read head 28 and directs the emitting light 82 from the sample 16 to a detector 36. The emitting light 82 contains two wavelength bands 82a and 82b which are both passed through the reflector 26. The first wavelength band 82a is reflected by a beamsplitter 88 toward the detector 36 via a first emission filter 90 (e.g., a bandpass filter). The second wavelength band 82b is passed by the beamsplitter 88, and reflected at a mirror 92 toward the detector 36 via a second emission filter 94 (e.g., a bandpass filter). The detector 36 is a dual channel detector which preferably has two detectors 96 and 98, preferably photomultiplier tubes which are stacked to form the dual channel detector. In addition, the cartridge 80 has a dual exit port 100 and 102, which is aligned with the detectors 96 and 98 via detector ports 104 and 106. The detector ports 104 and 106 may include collecting lenses that focus the quasi collimated emission light onto the active area(s) of the detector 36, which is typically smaller than the emission light 82 beam diameter.

Figure 4A:
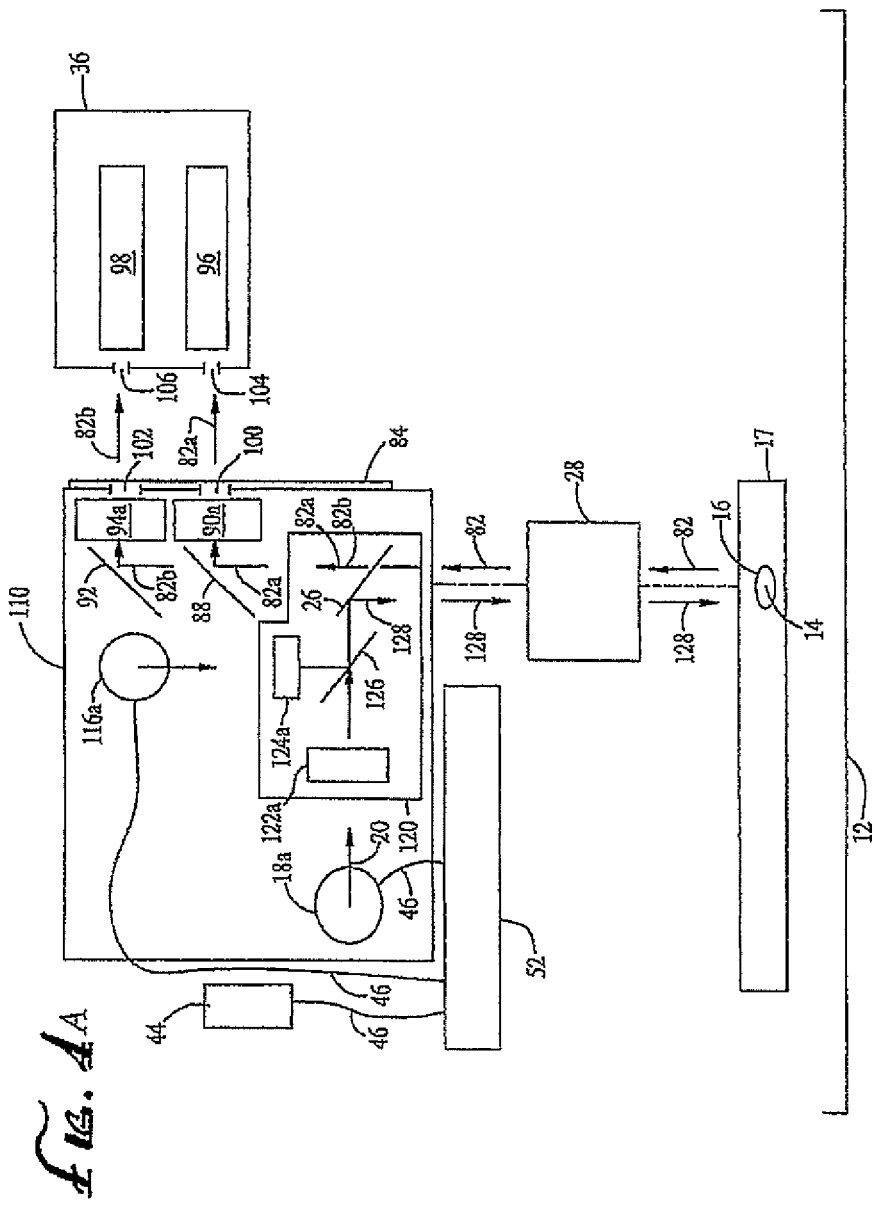
FIG. 4 is a schematic view of an example of a dual emission dual excitation cartridge according to an embodiment of the present invention.

Referring now to FIG. 4, another embodiment of the apparatus 12 for analyzing a target 14 in a sample 16 is shown. According to the embodiment shown in FIG. 4, the apparatus 12 has a dual emission dual excitation cartridge 110 that is equipped with a second light source 116. The cartridge 110 is designed to be removably engaged with apparatus 12 via the movable cartridge support 52. When light sources which can be pulsed are used, such as LEDs or laser diodes, the first and second light sources 18 and 116 may be electronically switched, and different wavelengths of light may be used to measure a sample. According to this embodiment, there is no need to mechanically switch between different wavelengths of light, which results in a saving of total measurement time.

According to the embodiment shown in FIG. 4, the apparatus 12 has a first light source 18 which produces a first exciting light 20 and a second light source 116 which produces a second exciting light 118. The apparatus 12 additionally has a power source 44 and the cartridge 110 has a coupler 46 for providing a current supply to light sources 18 and 116 from the power source 44. The dual emission dual excitation cartridge 110 has a first optical system 120 which has components, including a first excitation filter 122 and a second excitation filter 124, for directing the first and second exciting lights 20 and 118, respectively, to a beam combiner 126. The beam combiner 126 aligns the first and second exciting lights 20 and 118 to form a combined exciting light beam 128. The combined exciting light beam 128 is directed to the sample 16 via reflector 26 and read head 28. The sample 16, containing the target 14, produces an emitting light 82. The dual emission dual excitation cartridge 110 has a second optical system 84, as previously described with respect to FIG. 3, which receives the emitting light 82 from the read head 28 and directs the emitting light 82 from the sample 16 to detector 36.

In certain embodiments of the invention shown in FIG. 4, the dual emission dual excitation cartridge 110 is used to measure fluorescence polarization. According to this embodiment, the wavelengths of the first and second exciting lights 20 and 118 are essentially the same, and beam combiner 126 and beamsplitter 88 are polarizing cubes. The function of the second light source 116 is to determine the apparatus specific normalization factor for Fluorescence Polarization (G-Factor) by performing a calibration measurement.

Referring now to FIG. 5, another embodiment of the apparatus 12 for analyzing a target 14 in a sample 16 is shown. According to the embodiment shown in FIG. 5, the apparatus 12 has a dual excitation cartridge 130 that is equipped with a second light source 116. The cartridge 130 is designed to be removably engaged with apparatus 12. As described with respect to FIG. 4, when light sources that can be pulsed are used, the first and second light sources 18 and 116 may be electronically switched, and different wavelengths of light can be used to measure a sample. According to the embodiment of the cartridge 130 shown in FIG. 5, the second emission path (from FIG. 4) is omitted while the second excitation source is maintained. In a single emission configuration (preferable for matters of reducing costs), the dual excitation cartridge 130 enables the measurement of fluorescence polarization without mechanically moving polarization filters thereby saving valuable measurement time, as described in the following paragraph.

According to the embodiment shown in FIG. 5, the apparatus 12 has a first light source 18 which produces a first exciting light 20 and a second light source 116 which produces a second exciting light 118. The apparatus 12 additionally has a power source 44 and the cartridge 130 has a coupler 46 for providing a current supply to light sources 18 and 116 from the power source 44. The dual excitation cartridge 130 has a first optical system 120, as described with respect to FIG. 4, which has components, including a first excitation filter 122 and a second excitation filter 124, for directing the first and second exciting lights 20 and 118, respectively, to a polarizing beam splitter 132. The polarized light beam 134 is directed to a sample 16 via reflector 26 and read head 28. The read head 28 directs the exciting light 134 toward the sample 16. The dual excitation measurement may be performed quasi simultaneously, by alternating the polarization state of the beam, i.e., electronically switching between the first and second light sources 18 and 116. The sample 16, containing the target 14, produces an emitting light 32. The dual excitation cartridge 130 has a second optical system 34, as described with respect to FIG. 1B, which receives the emitted light 32 from the read head 28 and directs the emitted light 32 from the sample to the detector 36. The emitted light 32, received from the read head 28 is transmitted through a reflector 26 by a mirror 48 towards the cartridge exit 40, which interfaces with the detector 36. Before exiting the cartridge 130, the emitted light 32 is filtered through a filter 42 which is sandwiched with a polarization analyzing sheet 136. According to this embodiment, the G-Factor is determined using an assay standard.

According to another embodiment of the invention shown in FIG. 5, the dual excitation cartridge 130 may be used for a new type of microplate assay technology which uses two light sources in combination for photoactivation of a sample by one light source, followed preferably by a fluorescence measurement using the other light source. According to this embodiment, a first exciting light (e.g., exciting light 118 from light source 116) and a second exciting light (e.g., exciting light 20 from light source 18) are directed to the target 14 in succession, i.e., one after the other. The target 14 contains or is associated with a functional group having an inactivated state and an activated state, e.g. "caged" functional groups of biochemical starter reagents which are activated by flash photolysis. The first exciting light 118 is first directed to the target 14 to change the functional group associated with the target 14 from the inactivated state to the activated state (i.e., the functional group associated with the target 14 is photoactivated). The photoactivation of the functional group is followed by a fluorescence measurement which is accomplished by directing the second exciting light 20 to the target 14 associated with the functional group, which is in the activated state, to produce an emitting light 32 in response to the second exciting light 20. The second optical system 34 receives the emitting light 32 produced by the functional group on the target 14 and directs the emitting light 32 from the target 14 to the detector 36.

The above cartridge system used for photoactivation is described with respect to analyzing the target 14 in the sample 16 by a single emission fluorescence measurement. However, as will be understood by those of skill in the art by reference to this disclosure, the invention is not limited by the above described example, and other embodiments of the cartridge system employing a cartridge that is capable of photoactivating a target in a first step and reading an emission from the activated target in a second step are envisioned. For example, other fluorescence measurement configurations may be used according to the present invention, such as dual emission fluorescence (described with respect to FIG. 4, for example). Alternately, the target 14 in the sample 16 may be analyzed with other optical measurements such as absorbance or luminescence. For example, the target 14 in the sample 16 may be measured using absorbance. According to this embodiment, the cartridge has a dual light source, the first light source being used to activate the functional group on the target 14, as described with respect to FIG. 5, but the cartridge and apparatus are reconfigured for absorbance detection. In another example, the target 14 in the sample 16 may be measured using luminescence. According to this embodiment, the second light source in the cartridge is omitted and the first light source is used as an activating light source to activate the functional group on the target 14, as described with respect to FIG. 5, but the cartridge and apparatus are configured for luminescence detection.

The cartridge system used for photoactivation of a sample has several advantages over other analogous systems that employ reagent injection technology such as (i) photoactivation does not involve reagent injection, which imposes some risk of instrument contamination due to aerosol build up, splashes onto optics, and/or leakage; (ii) photoactivation does not require mixing of injected reagents, which can have incomplete mixing, and a lack of reproducibility; (iii) caged starter reagents may be brought right into living cells in order to trigger a reaction within a cell by external optical means. Such reactions cannot be triggered by the physical injection of starter reagents into the sample which contains such cells.

Figure 6B:
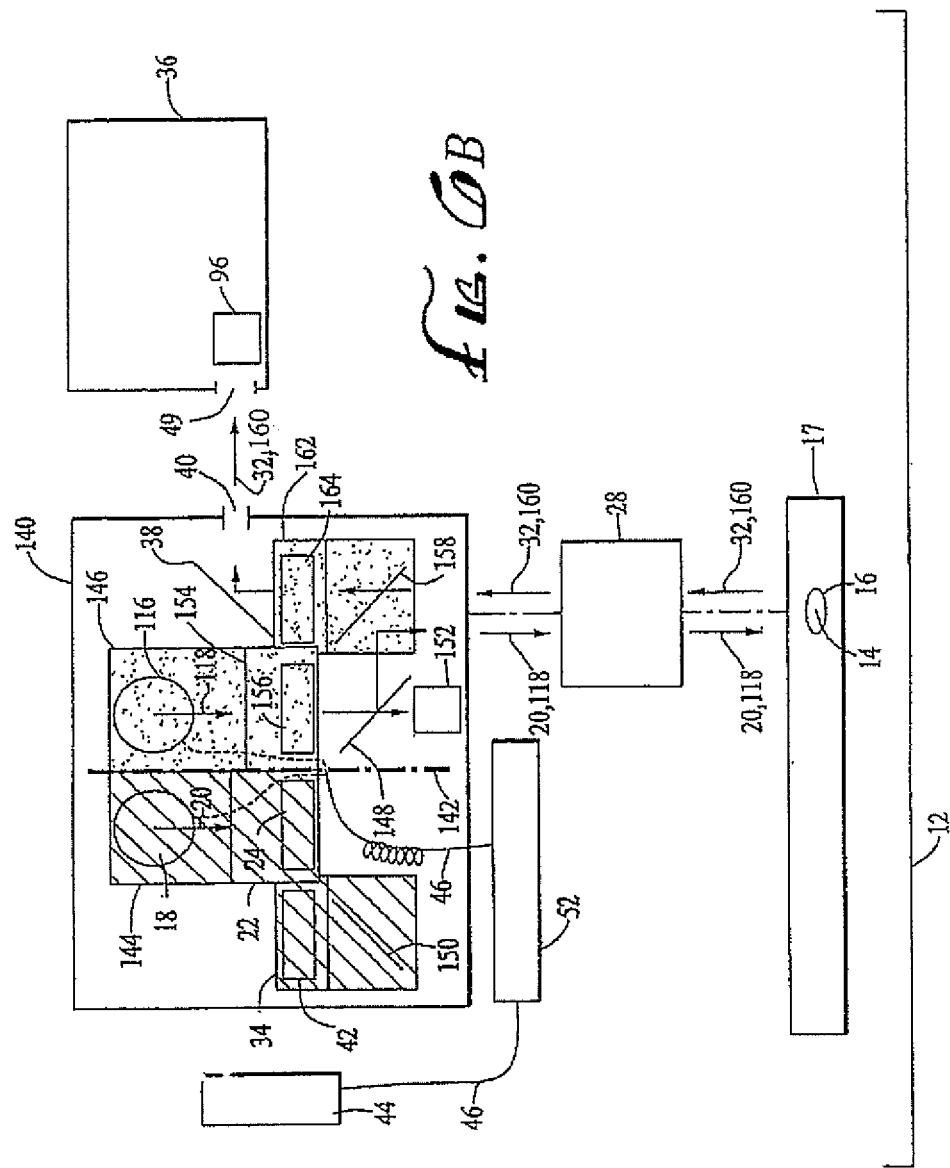

Referring now to FIG. 6A and FIG. 6B, another embodiment of the apparatus 12 for analyzing a target 14 in a sample 16 is shown. As shown in FIG. 6A and FIG. 6B, the apparatus 12 has a multi-purpose cartridge 140 that is equipped with multiple sections, or chambers, each section being configured for a particular spectroscopic application. The multi-purpose cartridge 140 may be equipped with multiple sections (e.g., 5 or 6), each chamber having an application specific set of light sources and/or optical systems that correspond to a particular application. In an alternative embodiment, a section (i.e., chamber, or section of the support) may be configured without a light source to provide a luminescence channel, i.e., luminescence light collected by the read head 28 is forwarded through a section of the cartridge 140 to the detector 36.

According to the embodiment shown in FIGS. 6A and 6B, the multi-purpose cartridge 140 has multiple light sources, each within a separate section, such as the first and second light sources 18 and 116, which are housed in first and second sections 144 and 146, respectively, as shown in FIGS. 6A and 6B. The multi-purpose cartridge 140 utilizes a revolver mechanism 142 that mounts each of the multiple sections, each section having an application specific set of optical systems, which correspond to the light source within a particular section e.g., each section houses excitation and emission filters, and a beam splitter for each different light source. The apparatus 12 additionally has a power source 44 and the multi-purpose cartridge 140 has a coupler 46 for providing a current supply to the multiple sections and light sources, such as light sources 18 and 116, from the power source 44 and is designed to be removably engaged with apparatus 12. According to the embodiment shown in FIGS. 6A and 6B, the power source 44 is coupled to light sources 18 and 116 by the coupler 46, as described with respect to FIGS. 1B and 1C. Inside the cartridge 140, between the cartridge plug and the light source control board 68 (shown in FIG. 2), the coupling continues with the help of a flat cable that coils up or uncoils again while the support 142 rotates.

As shown in FIGS. 6A and 6B, the multi-purpose cartridge 140 has a movable support 142 (e.g., a revolver-type mechanism), which mounts the first light source 18 and corresponding optics onto a first section 144 (i.e., a chamber) of the cartridge 140. The movable support 142 also mounts the second light source 116 and corresponding optics onto a second section 146 of the cartridge 140. The movable support 142 also mounts other sections e.g., sections 3, 4, 5, or more (not shown) onto the cartridge 140. A particular application provided by the first section 144 or second section 146, or other sections of the cartridge 140, (e.g., a particular wavelength of exciting light, as determined by the light source 18 or 116, or optical system for a luminescence application) is selected by moving the desired light source 18 or 116 into an operating position within the cartridge 140, e.g., by rotating a revolver mechanism of the movable support 142 about the axis (dotted line). FIG. 6A shows the operating position for the first light source 18 and FIG. 6B shows the operating position for the second light source 116.

Referring again to FIG. 6A, the first section 144 of the multi-color cartridge 140 comprises a first light source 18, which produces a first exciting light 20 (preferably collimated), and a first optical system 22, which has components, including a first excitation filter 24, for directing the first exciting light 20 to a partially reflecting mirror 148 and then to a dichroic beamsplitter 150 toward the read head 28. Prior to passing through the dichroic beamsplitter 150, a portion of the first exciting light 20 passes the partially reflecting mirror 148 and is measured by a detector 152, such as a photodiode, as previously described with respect to FIG. 2. The first exciting light 20 is directed to a sample 16 via a read head 28. The sample 16, containing the target 14, produces an emitting light 32. The first section 144 of the cartridge 140 has a second optical system 34, which receives the emitting light 32 from the read head 28 and directs the emitting light 32 from the sample 16 to the detector 36 via a filter 42, and a reflector 38, through the cartridge exit 40, which interfaces with the detector 36.

Referring again to FIG. 6B, the second section 146 of the multi-color cartridge 140 comprises a second light source 116, which produces a second exciting light 118 (preferably collimated), and a third optical system 154, which has components, including a first excitation filter 156, for directing the second exciting light 118 to a partially reflecting mirror 148 and then to the dichroic beamsplitter 158, and toward the read head 28. Prior to passing through the dichroic beamsplitter 158, a portion of the second exciting light 118 passes the partially reflecting mirror 148 and is measured by the detector 152, as previously described with respect to FIG. 2. The second exciting light 118 is directed to a sample 16 via a read head 28. The sample 16, containing the target 14, produces a second emitting light 160. The second section 146 of the cartridge 140 also has a fourth optical system 162, which receives the second emitting light 160 from the read head 28 and directs the second emitting light 160 from the sample 16 to the detector 36 via a filter 164, and the reflector 38, through the cartridge exit 40, which interfaces with the detector 36.

Figure 7:
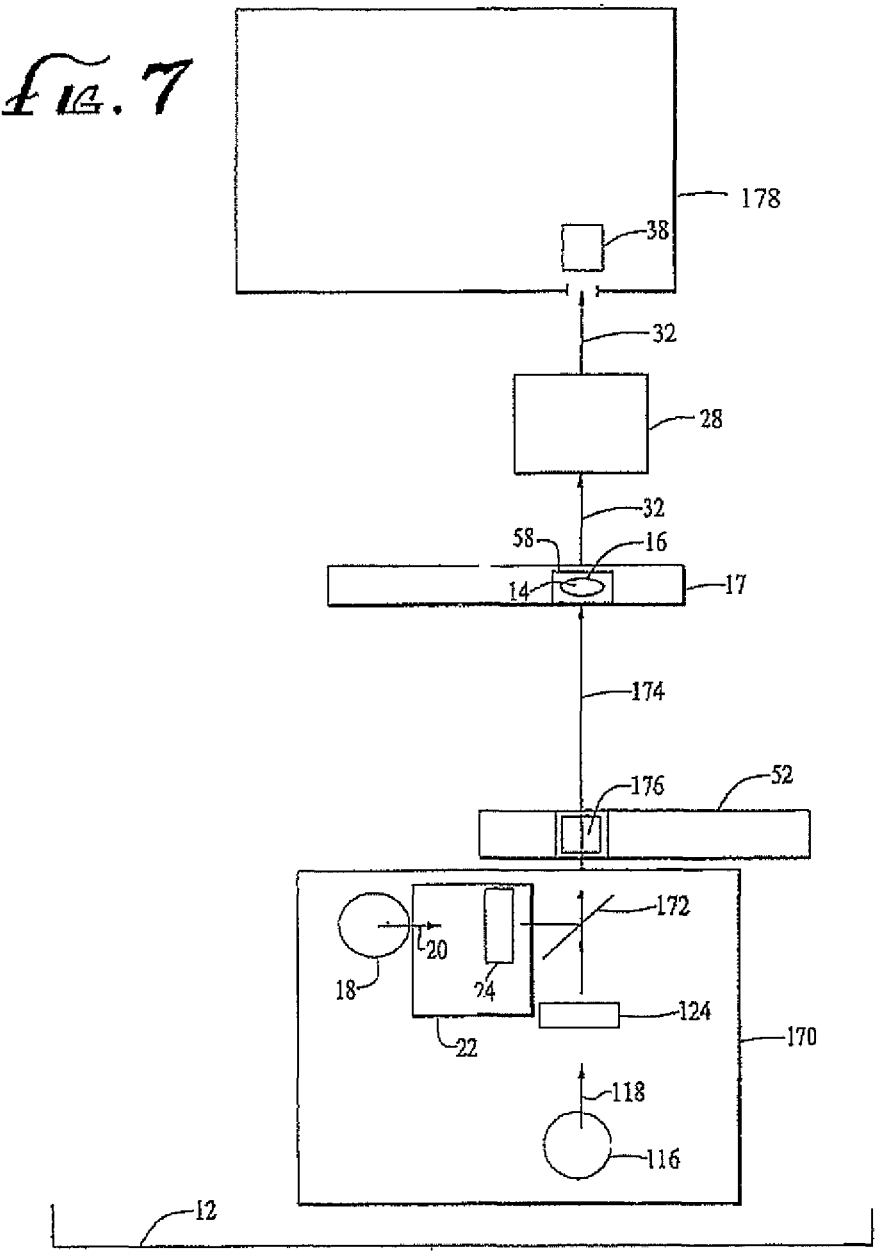
FIG. 7 is a schematic view of an example of a dual wavelength absorbance cartridge according to an embodiment of the present invention.

Referring now to FIG. 7, another embodiment of the apparatus 12 for analyzing a target 14 in a sample 16 is shown. According to the embodiment shown in FIG. 7, the apparatus 12 has a dual wavelength absorbance cartridge 170 that is equipped with first and second light sources 18 and 116, respectively. The apparatus 12 additionally has a power source 44 and the dual wavelength absorbance cartridge 170 has a coupler 46 for providing a current supply to light sources 18 and 116 from the power source 44. The dual wavelength absorbance cartridge 170 is designed to be removably engaged with apparatus 12.

As shown in FIG. 7, the dual wavelength absorbance cartridge 170 comprises first light source 18, which produces a first exciting light 20 (preferably collimated), and a first optical system 22, which has components, including a first excitation filter 24, for directing the first exciting light to a beam combiner 172 and then toward the sample 16. For absorbance applications, the beam is collimated to a smaller diameter than for fluorescence applications, and the excitation filters typically feature a smaller bandpass (i.e., narrower). For dual wavelength measurements, the dual wavelength absorbance cartridge 170 comprises a second light source 116, which produces a second exciting light 118, which is passed through a filter 124 and is aligned with the first exciting light 20 with help of the beam combiner 172 to produce a combined exciting light beam 174. The combined exciting light beam 174 is then passed through the cartridge support 52, via an aperture 176 (i.e., a window or light transparent section of the cartridge support 52) and focused into the sample 16, which is positioned on the sample support 17, via aperture 58. The dual wavelength measurement may be performed quasi simultaneously, by alternating the color of the combined beam 174, i.e., electronic switching between the first and second light sources 18 and 116. Emitting light 32 transmitted through the sample is collected by a read head 28 and focused onto an absorbance detector 178, containing, for example, a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

Referring now to FIG. 8, another embodiment of the apparatus 12 for analyzing a target 14 in a sample 16 is shown. According to the embodiment shown in FIG. 8, the apparatus 12 has a wide band light source cartridge 180 that is equipped with a first light source 18, which preferably is a wide band light source 182, such as a Xenon flash lamp module. The apparatus 12 additionally has a power source 44 and the wide band light source cartridge 180 has a coupler 46 for providing a current supply to light source 18 from the power source 44. The wide band light source cartridge 180 is designed to be removably engaged with apparatus 12.

The wide band light source 182 is a light source that can provide an exciting light over a wide band of the Ultraviolet (UV), visible (VIS), and near infrared (NIR) electromagnetic spectrum, (i.e., light having a wavelength from about 200 nm to about 1000 nm). Preferably, a Xenon flash lamp module is used as the wide band light source 182 because of the high intensity over the desired wavelength operating range. The flash mode is selected for its lower heat dissipation when compared with a constant Xenon Arc Discharge lamp.

According to the embodiment shown in FIG. 8, the wide band light source cartridge 180 comprises a first light source 18 includes a wide band light source 182. The wide band light source 182 produces an exciting light 20, which exits slit 184 of the wide band light source 182 and is directed (via a reflector 186) onto a wavelength selector 188, such as a monochromator grating that disperses the exciting light 20 (different wavelengths into different angles). A mirror 190 maps the different angles (wavelengths) onto different positions across the monochromator's exit slit 192, shown as a fan of rays indicated by dotted lines in FIG. 8. The wavelength of exciting light 198 (non dotted line) transmitted through the slit 192 is selected by rotating the wavelength selector 188. Further functions housed in the cartridge 180 are beam shaping optics 194, order sorting filters 196 (to remove unwanted contamination of the desired beam wavelength with light from other than first order grating diffraction), sitting on a filter wheel, and a partially reflecting mirror 64 and photodiode 62 for monitoring the intensity of the exiting beam, such as described with respect to FIG. 2. After exiting the wide band light source cartridge 180, the combined exciting light beam 198 is passed through the cartridge support 52 via aperture 176 and then focused onto the sample 16, which is positioned on the sample support 17, via aperture 58. Emitting light 32 transmitted through the sample 16 is collected by a read head 28 and focused onto an absorbance detector 178, such as a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

According to the present invention, any of the above described cartridges having an exciting light source, such as the cartridges shown in FIGS. 3-8 may be controlled by the electronic measurement circuitry 68 and corresponding detector 62, apparatus controller 74, and feedback loops 66 and 72 described with respect to FIG. 2.

Referring now to FIG. 9, a luminescence cartridge 200 for use in an apparatus 12 for analyzing a target 14 in a sample 16 is shown. As shown in FIG. 9, the cartridge 200 comprises an integrated read head 202 and a driver 204, which moves the read head 202 in the direction indicated by arrow 205 into a detection position above the sample 16 when receiving emitting luminescent light 206 from the sample 16. The integrated read head 202 can also be moved by the driver 204 away from the sample 16 into a latent position when the luminescence cartridge 200 is not in use, or the apparatus 12 is being loaded with a new sample support 17. Preferably, the read head 202 is fully retractable into the cartridge 200, and also preferably, for reasons of saving measurement time, the read head 202 will not move up and down when moving from the one sample 16 to the next, but will stay in proximity above the sample support 17, when moving from one sample 16 to the next sample. The integrated read head 202 is retracted when the sample support 17 is moved in or out of the apparatus 12 in order to avoid parts of the sample support carrier (not shown) that extend beyond the upper sample support level.

Preferably, the integrated read head 202 is a rigid light guide that receives emitting luminescent light 206 at a proximal end 208 of the integrated read head 202 from a position above the sample holder 17 and sample 16. The emitting luminescent light 206 then exits the integrated read head 202 at a distal end 210 of the integrated read head 202 and is collimated by a lens 212 to produce a collimated light beam 218.

According to the embodiment of the luminescence cartridge 200 shown in FIG. 9, the apparatus 12 and luminescence cartridge 200 are configured for a bioluminescence resonance energy transfer (BRET) type measurement, where luminescence light is composed of two wavelength bands (e.g., a dual emission cartridge configuration) which is detected simultaneously with a dual channel detector. The dual emission cartridge and dual channel detector are further described with respect to FIGS. 3 and 4. As shown in FIG. 9, the collimated emitting luminescent light beam 218 is redirected with a reflector 214 toward a dichroic beamsplitter 88 via a lens 216 and separated into two wavelength bands 218a and 218b. The first wavelength band 218a is passed or transmitted by a beamsplitter 88 toward the detector 36 via a first emission filter 90 (e.g., a bandpass filter). The second wavelength band 218b is reflected by the beamsplitter 88, and reflected at the mirror 92 toward the detector 36 via a second emission filter 94 (e.g., a bandpass filter). The detector 36 is preferably a dual channel detector having two detectors 96 and 98 (e.g., photomultiplier tubes) stacked to form the dual channel detector. In addition, the luminescence cartridge 200 has a dual exit port 100 and 102, which is aligned with the detectors 96 and 98 via detector ports 104 and 106.

In an alternative embodiment, for a wider class of luminescence measurements, which do not require simultaneous measurement of two wavelength bands, the cartridge 200 may be simplified by omitting the beamsplitter 88, mirror 92, and second emission filter 94.

FIG. 9A is a schematic view of an example of a luminescence cartridge 900 according to another embodiment. The luminescence cartridge 900 may be utilized in conjunction with the apparatus 12 as a system for analyzing a target 14 in a sample 16. Like the cartridges described above and illustrated in FIGS. 1A-9, the luminescence cartridge 900 is designed to be removably engaged with the apparatus 12 by loading (mounting, installing) the luminescence cartridge 900 on the cartridge support 52, and may be replaced or exchanged with other cartridges of the same of different type.

The luminescence cartridge 900 includes a cartridge housing 904 that is sized and configured to be removably loaded or mounted on the cartridge support 52. The luminescence cartridge 900 also includes an integrated luminescence detector 908 that is movable through an opening 220 of the cartridge housing 904. In typical embodiments, the luminescence detector 908 is linearly movable in a reciprocating manner as indicated by an arrow 205, i.e., alternately toward the cartridge housing 904 (and thus away from the sample carrier 54) to selected retracted positions and away from the cartridge housing 904 (and thus toward the sample carrier 54) to selected extended positions. Depending on the design and location of the cartridge support 52, the cartridge support 52 may also include an opening to accommodate the extension of the luminescence detector 908 toward the sample carrier 54, as schematically shown in FIG. 9A. To actuate and control the movement of the luminescence detector 908, the luminescence cartridge 900 includes a detector driver (or drive mechanism, or drive assembly) 204 that is coupled to the luminescence detector 908. The detector driver 204 may be mounted at the cartridge housing 904 in any suitable manner, and in typical embodiments is contained within the interior of the cartridge housing 904. As appreciated by persons skilled in the art, the detector driver 204 may have any configuration suitable for moving (i.e., retracting and extending) the luminescence cartridge 900 to any selected position relative to the cartridge housing 904 (and thus relative to the sample carrier 54 and any selected sample 16 supported by the sample carrier 54). In a typical embodiment, the detector driver 204 includes a motor (e.g., a micromotor) coupled to a linkage or transmission that is in turn coupled to the luminescence detector 908. The detector driver 204 may include bearings or other appropriate components necessary for facilitating reliable and accurate actuation of the luminescence detector 908. The linkage or transmission may have any configuration suitable for converting the rotational movement of the motor to linear movement of the luminescence detector 908. For example, the linkage or transmission may include a set of gears such as a rack and pinion, a set of bevel gears, a worm and worm gear, etc.

To facilitate loading of luminescence cartridge 900 on the cartridge support 52 and subsequent removal therefrom, and to prevent damage to the luminescence detector 908 during loading and removal, the luminescence detector 908 may be fully retractable within the cartridge housing 904 by the detector driver 204 such that no part of the luminescence detector 908 extends outside of the cartridge housing 904. The luminescence detector 908 may also be moved to the fully retracted position while the cartridge support 52 is moving the luminescence detector 908 (and any other cartridges loaded on the cartridge support 52) to different positions within the apparatus housing 50. However, the luminescence detector 908 typically does not need to be moved when acquiring luminescence data from multiple samples 16. That is, as noted elsewhere multiple samples 16 may be provided at individual sites of a sample support 17, such as in different wells of a multi-well plate that is supported on the sample carrier 54. The luminescence detector 908 may be moved to a desired distance from the first sample 16 which, in the illustrated "top reading" example, is a desired elevation above the first sample 16. This desired distance will typically be the same for all samples 16 contained on the sample support 17. Thus, the position of the luminescence detector 908 typically does not need to be adjusted as the sample carrier 54 moves the sample support 17 to sequentially align one sample 16 after another with the luminescence detector 908 to take sequential luminescence readings.

In the illustrated embodiment, the luminescence detector 908 is generally elongated between a proximal end and a distal end. In typical embodiments, the luminescence detector 908 is cylindrical with a circular cross-section, although in other embodiments may have a polygonal (e.g., rectilinear) cross-section. As an example, the luminescence detector 908 may have a length of 75 mm and an outer diameter of 11 mm. It will be understood, however, that this example is not limiting and the luminescence detector 908 may have any size suitable for use with the luminescence cartridge 900 and associated apparatus 12. The distal end (or optical input end) serves as the optical input of the luminescence detector 908 at which luminescent light 206 emitted from the sample 16 is received. The proximal end in typical embodiments remains in the cartridge housing 904 throughout the extent of travel of the luminescence detector 908. The luminescence detector 908 includes an active detector component 912 that receives the luminescent light 206 via the optical input.

An advantage of integrating the luminescence detector 908 with the cartridge housing 904, as opposed to utilizing the output detector 36 located external to the luminescence cartridge 900 (as in, for example, FIG. 9), is that it enables the luminescence detector 908 to be configured for dedicated operation in conjunction with luminescence measurements. That is, unlike the externally located output detector 36, the integrated luminescence detector 908 does not need to accommodate the operation of any other removable cartridge that might be loaded in the apparatus 12. Because the luminescence detector 908 is not utilized for a broader variety of data acquisitions (e.g., absorbance, fluorescence), the configuration of the luminescence detector 908 may be optimized for operation specifically with luminescence measurements. Thus, for example, the luminescence detector 908 may be selected to have maximum sensitivity to the wavelength ranges typically associated with the luminescent light 206. As an example, the wavelength of the luminescent light 206 may range from visible wavelengths to about 800 nm.

Examples of suitable detector components 912 include, but are not limited to, photomultiplier tubes (PMTs) and photodiodes. For many applications, a PMT may be considered to be a preferred type of detector component 912 in view of its relatively low cost, high gain, high frequency response, large numerical aperture, and capability for single photon counting. As appreciated by persons skilled in the art, the PMT typically includes a series of electrodes enclosed in an evacuated glass tube, for example a photocathode located at the optical input end of the tube, followed by a series of dynodes, and followed by an anode. One or more focusing electrodes may be located between the photocathode and the first dynode. The anode is in signal communication with an electrical connector located at the output end of the glass tube, typically via a sealed electrical feed-through structure. In the illustrated embodiment, the luminescence detector 908 also includes an outer detector housing 916 that encloses and thus protects the detector component 912. The detector housing 916 provides a robust structure to which the detector driver 204 may be directly coupled.

At the proximal end, the luminescence detector 908 may include an electrical connector 920 (e.g., contacts, terminals, pins, wire support, etc.), which may be part of or mounted to the detector housing 916. The detector component 912 is in signal communication with the electrical connector 920 to enable measurement signals generated by the luminescence detector 908 to be outputted to signal processing circuitry (e.g., data acquisition circuitry) located external to the luminescence cartridge 900. In some embodiments, the detector component 912 may be about as long as the detector housing 916 such that the electrical connector of the detector component 912 is in direct contact with (or is the same as) the illustrated electrical connector 920.

In some embodiments, the luminescence detector 908 may include an adjustable iris (or iris assembly) 924 mounted to the detector housing 916 at the distal (optical input) end. The adjustable iris 924 may have any configuration suitable for adjusting the numerical aperture of the luminescence detector 908, and thus the range of angles over which the luminescence detector 908 can receive the luminescent light 206 emitted from the sample 16. The adjustable iris 924 is thus useful for maximizing the amount of luminescent light 206 received from the target sample 16 and for minimizing the stray light received from adjacent samples 16 (e.g., samples 16 in adjacent wells of a multi-well plate). The adjustable iris 924 is also useful for accommodating different types and geometries of sample supports 17, for example different multi-well plate formats (e.g., 96-well, 384-well, 1536-well, etc.), thereby ensuring that light input is optimized for different sample supports 17. Adjustment of the iris 924 may also be done in combination with adjustment of the distance of the optical input end of the luminescence detector 908 from the sample 16 to optimize light input. Various types of adjustable irises 924 are known to persons skilled in the art. As an example, the adjustable iris 924 may include a set of overlapping shutters (not shown) that are movable relative to each other to define an opening of variable diameter through which the luminescent light 206 passes into the luminescence detector 908. The adjustable iris 924 may also include an actuating device (not shown) that moves the shutters. The actuating device may be manual or automated. An automated actuating device may be in signal communication with the electrical connector 920 of the detector housing 916 to receive power from the power source 44.

As indicated earlier in this disclosure, loading removable cartridges at the cartridge support 52 may entail coupling the removable cartridges with the cartridge support 52 in such a way as to place certain components of the removable cartridges in signal communication with the power source 44 and/or the electronic controller (or system controller, or main apparatus controller) 74, as appropriate. As an example, schematically illustrated in FIG. 9A, the luminescence cartridge 900 includes a first electrical connector 942 and the cartridge support 52 includes a second electrical connector 944. The luminescence cartridge 900 may be removably engaged with the cartridge support 52 by removably engaging or coupling the first electrical connector 942 with the second electrical connector 944. For this purpose, the first electrical connector 942 and the second electrical connector 944 may have any suitable complementary configurations (e.g., plugs and sockets, male and female connectors, etc.). The detector component 912, and the adjustable iris 924 if provided and if powered, may communicate with the first electrical connector 942 via one or more wires or a ribbon cable 952. The wire(s) or ribbon cable 952 should be of sufficient length to accommodate the travel of the luminescence detector 908 within the cartridge housing 904. The detector driver 204 may likewise communicate with the first electrical connector 942 via a wire 954. The second electrical connector 944 in turn communicates with the power source 44 and the system controller 74, as schematically indicated by respective dashed lines interconnecting the cartridge support 52 with the power source 44 and the system controller 74. The dashed lines may represent any suitable communication link (wired or wireless). By this configuration, installing the luminescence cartridge 900 at the cartridge support 52 may place the detector driver 204 and adjustable iris 924 in signal communication with the power source 44 and the system controller 74, and the detector component 912 in signal communication with the system controller 74, all via the coupling made between the first electrical connector 942 and the second electrical connector 944. Additional dashed lines in FIG. 9A depict communication between the power source 44 and the cartridge support 52 and the sample carrier 54, and between the system controller 74 and the cartridge support 52 and the sample carrier 54.

As also schematically illustrated in FIG. 9A, the system controller 74 may represent one or more modules configured for controlling, monitoring and/or timing various functional aspects of the apparatus 12 and the luminescence cartridge 900 and/or for receiving data or other signals from the apparatus 12 and the luminescence cartridge 900. In typical embodiments, the system controller 74 may include a main electronic processor 962 providing overall control, and may include one or more electronic processors configured for dedicated control operations or specific signal processing tasks. The system controller 74 may also include one or more memories and/or databases 964 for storing data and/or software. The system controller 74 may also include a computer-readable medium 966 that includes instructions for performing any of the methods disclosed herein. The functional modules of the system controller 74 may comprise circuitry or other types of hardware (or firmware), software, or both. In the illustrated example, the modules may include one or more of the following: signal processing (or data acquisition) circuitry 968 for receiving measurement signals from the luminescence detector 908, a detector drive controller 970 for controlling the movement of the luminescence cartridge 900, an iris controller 972 for controlling the adjustment of the iris 924, a cartridge support drive controller 974 for controlling the movement of the cartridge support 52, and a sample carrier drive controller 976 for controlling the movement of the sample carrier 54. The system controller 74 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 74 may include an operating system (e.g., Microsoft Windows® software) for controlling and managing various functions of the system controller 74.

In one embodiment of a method for analyzing a target 14 in a sample 16, the luminescence cartridge 900 is loaded (or installed) on the cartridge support 52 to position the luminescence cartridge 900 in the apparatus housing 50 (FIG. 1B). Loading may include opening a panel or door of the apparatus 12 (such as may be located on a side of the apparatus housing 50) to access the cartridge support 52. The cartridge support 52 may first be moved to a position at least partially outside the apparatus housing 50, and after the luminescence cartridge 900 is loaded on the cartridge support 52, the cartridge support 52 may then be moved back into the apparatus housing 50 with the luminescence cartridge 900 loaded thereon. Loading may also entail coupling the first and second electrical connectors 942 and 944 as described above to establish paths for transmitting power, data and control signals. Before or after loading the luminescence cartridge 900, the sample 16 is loaded on the sample carrier 54, typically by first loading the sample 16 on a sample support 17 and in turn loading the sample support 17 on the sample carrier 54. A plurality of samples 16 may be loaded together on an appropriate sample support 17 such as a multi-well plate. Ultimately, the cartridge support 52 and the sample support 17 will be positioned relative to each other such that the sample 16 will be aligned with the luminescence detector 908, either above or below the luminescence detector 908 depending on the configuration. In the present context, "aligned" means optically aligned, i.e., positioned so as to establish an optical path sufficient for luminescence data acquisition from the sample 16.

The luminescence detector 908 is then moved toward the sample 16 until its optical input end reaches a desired distance (reading position) from the sample 16. An advantage of the integrated luminescence detector 908 is that it may be moved very close to the sample 16 to be interrogated, thus maximizing light collection from the target sample 16 and minimizing stray light collection from adjacent samples. In some embodiments, the luminescence detector 908 is equipped with an iris 924 that may be adjusted as needed in preparation for data acquisition. At the reading position, the luminescence detector 908 receives (collects) the luminescent light 206 emitted from the sample 16. The luminescence detector 908 converts these optical signals into electrical signals (detector signals, or measurement signals) and transmits the electrical signals to the signal processing circuitry 968 of the system controller 74. In the case of multiple samples 16, the sample carrier 54 may be moved to sequentially align each additional sample 16 with the luminescence detector 908, whereby luminescence measurements are taken from all samples 16 sequentially.

At the completion of making the luminescence measurements, the luminescence cartridge 900, being a modular or removable cartridge as described throughout the present disclosure, may then be removed from the cartridge support 52, and thereafter replaced with another luminescence cartridge 900 or different type of removable cartridge as desired. Before moving the cartridge support 52 through the apparatus housing 50 as needed to remove the luminescence cartridge 900, the luminescence detector 908 may be retracted to a position completely inside the cartridge housing 904 to protect the luminescence detector 908 during movement.

The luminescence cartridges 200 and 900 described above may be utilized in various types of luminescence measurement techniques, including glow luminescence and flash luminescence. These types of measurements may be applied, for example, in conjunction with apoptosis studies, cAMP (cyclic adenosine monophosphate) quantitation, GPCR (G protein-coupled receptor) ligand binding, and immunoassaying. Glow luminescence reagents (e.g., luciferase, luciferin) may be added to samples 16 before or after loading the sample support 17 on the sample carrier 54 and moving the sample carrier 54 into the apparatus housing 50. Dispensing devices suitable for controllably adding glow luminescence reagents to samples 16 are generally understood by persons skilled in the art, and may be manually operated or automated devices. A dispensing device may be a component of the apparatus 12, in which case it may be controlled by the system controller 74, or it may be a device separate from the apparatus 12. Flash luminescence reagents (e.g., aequorin or other photoprotein) may be dispensed by an injector provided with the apparatus 12 or an injector integrated with a removable cartridge. Examples of the use of luminescence cartridges 200 and 900 for flash luminescence are described below in conjunction with FIG. 14.

Referring now to FIG. 10, another embodiment of the invention, a cartridge system 220 for use in an apparatus 12 for analyzing a target in a sample (not shown) is provided. As shown in FIG. 10, the apparatus 12 has a cartridge support 232 (i.e., a slide mechanism or cartridge slider) which is configured to concurrently receive a multitude of different cartridges. According to this embodiment, a cartridge for a desired application, such as fluorescence, absorbance, or luminescence, is selected by the user and is selectively aligned by the apparatus 12 with the read head 28 and the output detector 36 by moving the selected cartridge into the analysis position A, along the direction indicated by arrow 234. In this manner, a single instrument may house several application cartridges at a time and an application may be selected by the user without the user performing a multitude of application specific adjustments to the instrument such as selecting the correct combination and adjustment of filters, beamsplitters, apertures, and lightguides, etc. for a given application.

Referring again to FIG. 10, the cartridge system 220 comprises a plurality of cartridges, each cartridge being removably engaged with the apparatus 12. Examples of cartridges that may be used in the cartridge system 220 are one or more of the cartridges described in FIGS. 1A-9A. Exemplary cartridges used in the cartridge system 220 are shown in FIG. 10 as cartridge 222, cartridge 224, cartridge 226, cartridge 228, and cartridge 230. However, a greater or fewer number of cartridges may be used in the cartridge system 220 and the cartridges need not have the same dimensions such that cartridges having more complex systems (and larger dimensions) or less complex systems (and smaller dimensions) may be used in the apparatus 12. The apparatus 12 has a cartridge support 232 (i.e., a slide mechanism or cartridge slider) which is configured to receive the cartridges (e.g., cartridges 222, 224, 226, 228, and 230) and align each of the cartridges with the detector 36 and read head 28.

In a preferred but not required embodiment, each cartridge has indicia, such as an electrically erasable programmable read-only memory, EEPROM, that indicates the type of detection that the cartridge can be used for and the corresponding parameters for the particular cartridge. Also preferably, the cartridge support 232 features a cartridge detector, such as a data line function, or an electronic bus system, that enables the instrument control software (not shown) to identify a cartridge's slot position (i.e., the position of the cartridge on the cartridge support 232) and recognize any application specific parameters stored in the cartridge's EEPROM.

In another preferred but not required embodiment, the cartridge support 232 dimensions are such that it can be moved through a front door or access panel of the apparatus housing and every cartridge position or "slot" on the cartridge support 232 can be accessed for installation or removal of a cartridge. More preferably, one cartridge is capable of being removed from the cartridge support 232 and exchanged with a second cartridge, or alternately, a new cartridge is installed in an empty slot on the cartridge support 232 without the use of mechanical tools, or with a simple mechanical tool, such as for releasing a fastening mechanism (e.g., a fastening clip).

In another preferred but not required embodiment, at least one of the cartridges in the cartridge system 220 has one or more light sources that produces an exciting light, such as the cartridges described with respect to FIGS. 1A-8. In another preferred but not required embodiment, at least one of the cartridges in the cartridge system 220 has an integrated read head and a driver (not shown), such as that described with respect to FIG. 9 for moving the read head. In some embodiments, at least one of the cartridges in the cartridge system 220 is a luminescence cartridge 900 such as described above and illustrated in FIG. 9A.

Referring now to FIG. 11, another embodiment of the invention, a top and bottom reading cartridge system 240 for use in an apparatus 12 for analyzing a target 14 in a sample 16 is provided. As shown in FIG. 11, the apparatus 12 has a first cartridge support 232 which supports a first cartridge 242 and a second cartridge support 244 which supports a second cartridge 246. The first and second cartridges 242 and 246 may be any of those described herein such as the cartridges described with respect to FIGS. 1-9, but preferably are configured for fluorescence applications. As noted above in the description relating to FIGS. 1B and 1C, the first cartridge support 232 and/or the second cartridge support 244 may be configured for supporting a plurality of cartridges, and for selectively aligning one or more of the cartridges with the read head 28 or 250 and/or the detector 36, as appropriate for carrying out a particular type of measurement.

According to the embodiment shown in FIG. 11, the first cartridge support 232 and first cartridge 242 are positioned above the sample support 17. The exciting light 20 from the first cartridge 242 is directed to the sample 16 through a first read head 28. The emitting light 32 from the sample 16 is then directed again through the first cartridge 242, by which the emitting light 32 is directed to the detector 36 as previously described herein, for example, with respect to FIGS. 1-6. The emitting light 32 may be split into one or more wavelength bands 32a and 32b as previously described. The second cartridge support 244 and second cartridge 246 are positioned below the sample support 17 and the exciting light 248 from the second cartridge 246 is directed to the sample 16 through a second read head 250. The emitting light 252 is then directed again through the second cartridge 246, where it is split into emitting lights 252a and 252b and relayed remotely to the detector 36. Preferably, light guides 254 and 256 relay the emitting light 252a and 252b from the bottom of the second cartridge 246 through an exit port (not shown) to the detector 36.

In some embodiments, a luminescence cartridge 200 or 900 such as described above and illustrated in FIG. 9 or 9A is loaded at the first cartridge support 232 and thus above the sample support 17 for top reading, or is loaded at the second cartridge support 244 and thus below the sample support 17 for bottom reading, or two luminescence cartridges 200 or 900 may be respectively loaded at the first cartridge support 232 and second cartridge support 244.

The design of the first and second cartridges 242 and 246 is independent of whether the cartridge is positioned either above or below the sample support 17. However, when the cartridge configuration shown in FIG. 11 is used, a movable detector port support 258 (e.g., a slide or selector wheel mechanism) is used which switches the detector 36 from seeing either emitting light 32a and 32b from the first cartridge 242 and first read head 28 or seeing emitting light 252a and 252b from the second cartridge 246 and second read head 250. The emitting light 252a and 252b exiting the light guides 254 and 256 is reflected into the detector 36 by mirrors 260a and 260b. The selection between the first and second cartridges 242 and 246 is done by moving the movable detector port support 258 along an axis 262 perpendicular to the detector 36. This embodiment is further detailed in FIG. 12.

Figure 12:
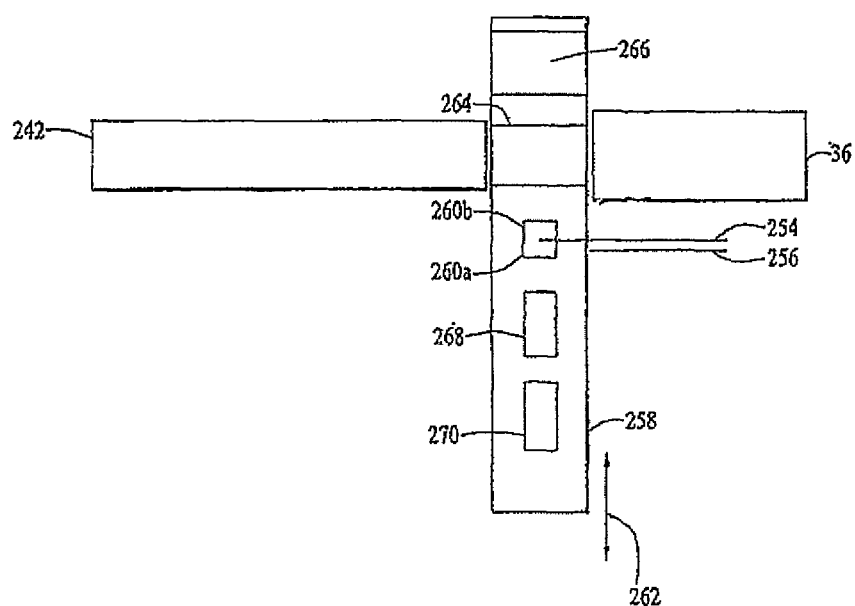
FIG. 12 is a schematic top view of the cartridge configuration shown in FIG. 11.

According to the embodiment shown in FIG. 12, the movable detector port support 258 is located in the gap between the exit of the first cartridge 242 and the entrance to the detector 36. The movable detector port support 258 houses an aperture 264 (e.g., a beam pass) which directs emitting light 32a and 32b from the first cartridge 242 and a beam stop/shutter 266 which protects the detector 36 when the instrument front door is opened, such as for maintenance or to exchange a cartridge. The movable detector port support 258 may also be equipped with light attenuating filters 268 and 270 which enable the system to analyze a signal that is too strong for the detector 36. The movable detector port support 258 may also be equipped with a constant low power light source in order to monitor the function and performance of the detector 36 over longer periods of operation (not shown). The light source resident in the detector port support 258 is built from a LED and stabilized by feedback from a photodiode, as described for a cartridge with respect to FIG. 2. The LED output is attenuated down to levels acceptable to the detector 36 by help of a diffusing glass. Another position along the movable detector port support 258 may house mirrors 260a and 260b that reflect the emitting light 252a and 252b exiting the light guides 256 and 254 from above and below the movable detector port support 258. Emitting light 252a and 252b exiting the light guides 256 and 254 can enter the detector 36 when the position of the light guides 256 and 254 on the detector port support 258 is aligned with the detector 36.

As is evident from FIGS. 2 and 8, in certain embodiments a removable cartridge may include a detector. As is also evident from FIGS. 1C, 7, 8 and 11, in certain embodiments systems implementing absorbance measurements such as illustrated in FIGS. 1C, 7 and 8 may be adapted to the top and bottom cartridge configuration illustrated in FIG. 11. As examples, the absorbance cartridge 10 shown in FIG. 1C, the dual wavelength absorbance cartridge 170 shown in FIG. 7, or the wide band light source absorbance cartridge shown in FIG. 8 may be loaded onto the second (bottom) cartridge support 244 shown in FIG. 11. In a further example, the absorbance detector 178 shown in FIGS. 7 and 8 may be provided in a removable cartridge that is loaded onto the first (upper) cartridge support 242 shown in FIG. 11. In such embodiments, the sample support 17, first cartridge support 242 and/or second cartridge support 244 may include apertures 58, 176 (FIGS. 7 and 8) as needed, and one or both read heads 28 and 250 may be bypassed as needed.

Figure 13:
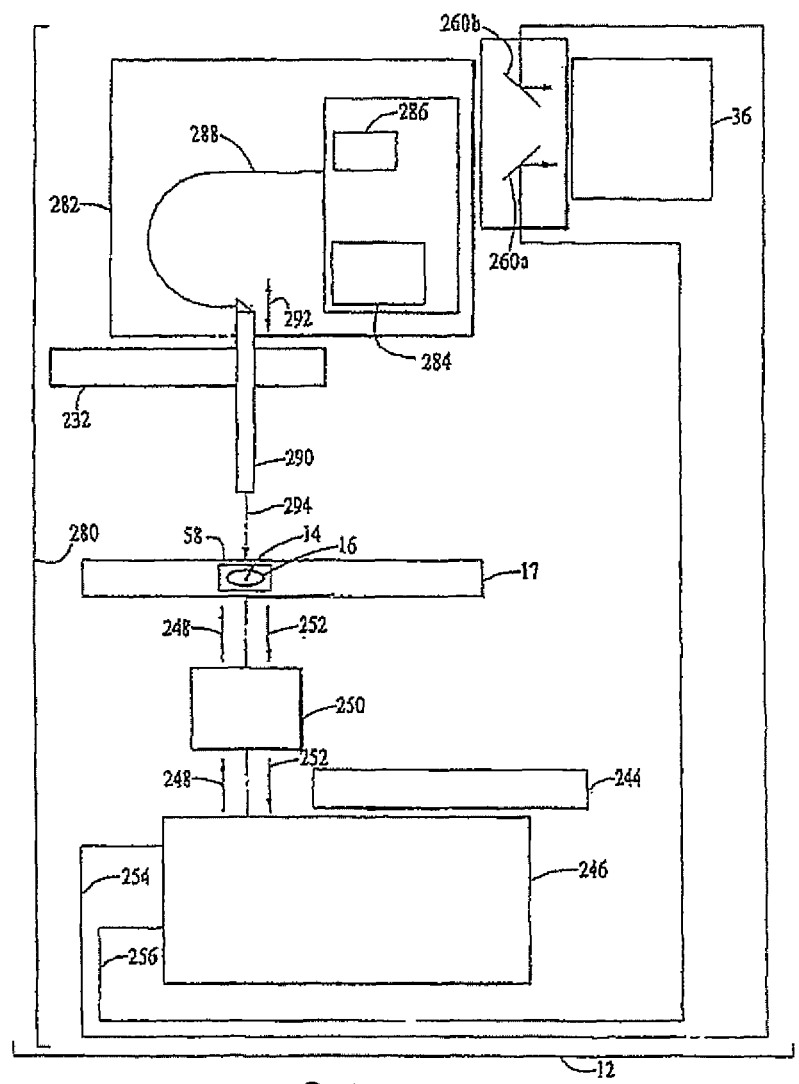
FIG. 13 is a schematic view of an example of a flash fluorescence cartridge system according to an embodiment of the present invention.

Referring now to FIG. 13, another embodiment of the invention, a flash fluorescence cartridge system 280 for use in an apparatus 12 for analyzing a target 14 in a sample 16 is provided. The flash fluorescence cartridge system 280 has an injector cartridge (i.e., the first cartridge 282) that may be used for flash fluorescence applications, which require injection of a starter reagent in combination with immediate fluorescence reading.

For typical flash fluorescence applications, clear bottom microplates are frequently used as the sample support 17 (i.e., a sample support having an aperture 58) such that injection of the reagent occurs from above the well and fluorescence is measured simultaneously from below the sample holder 17. Accordingly, FIG. 13 uses the top and bottom reading cartridge configuration, which has been described with respect to FIG. 11. According to the embodiment shown in FIG. 13, an injector cartridge 282 is installed as the first cartridge (i.e., the upper cartridge) on the first cartridge support 232. A second cartridge 246 is positioned on a second cartridge support 244. The second cartridge 246 may be any of those described herein such as the cartridges described with respect to FIGS. 1-6 and 13, but configured for a fluorescence application. As noted again, the first cartridge support 232 and/or the second cartridge support 244 may be configured for supporting a plurality of cartridges, and for selectively aligning one or more of the cartridges with the read head 250 and/or the detector 36, as appropriate for carrying out a particular type of measurement.

As shown in FIG. 13, the first cartridge 282 features a reagent reservoir 284, a pump 286, and a tubing system 288 connected to a nozzle 290 (preferably rigid). The nozzle 290 can be driven down from within the first cartridge 282 to approach the sample support 17 from above, as shown by arrow 292. The nozzle 290 is aligned with a sample 16 and read head 250 and reagent 294 is delivered to the sample 16 via the nozzle 290. Exciting light 248 and emitting light 252 is directed to the sample 16 and subsequently to the detector 36 as described with respect to FIG. 11. Sample measurement may take place before, during, and after injection of reagent 294.

Using an injector module that can be easily removed under routine operating conditions, such as the injector cartridge described herein, provides several advantages. The injector cartridge and external docking station may also be used as a precision dispenser apparatus. In addition, the cartridge's tubing system can be easily rinsed/cleaned by the customer and primed, i.e., floated, thereby removing bubbles, with the reagent outside of the instrument enclosure. This may occur with the injector cartridge still plugged into the cartridge support, but with the cartridge support moved through the instrument door and having a waste reservoir placed underneath. Priming may also occur with the injector cartridge removed from the cartridge support and plugged into a docking station. Both strategies reduce the risk of accidentally floating the interior of the apparatus with reagent. Also, the output of the injector cartridge can be calibrated for the customer's solvents at the customer site using an external docking station mounted on top of weighing scales.

Figure 14:
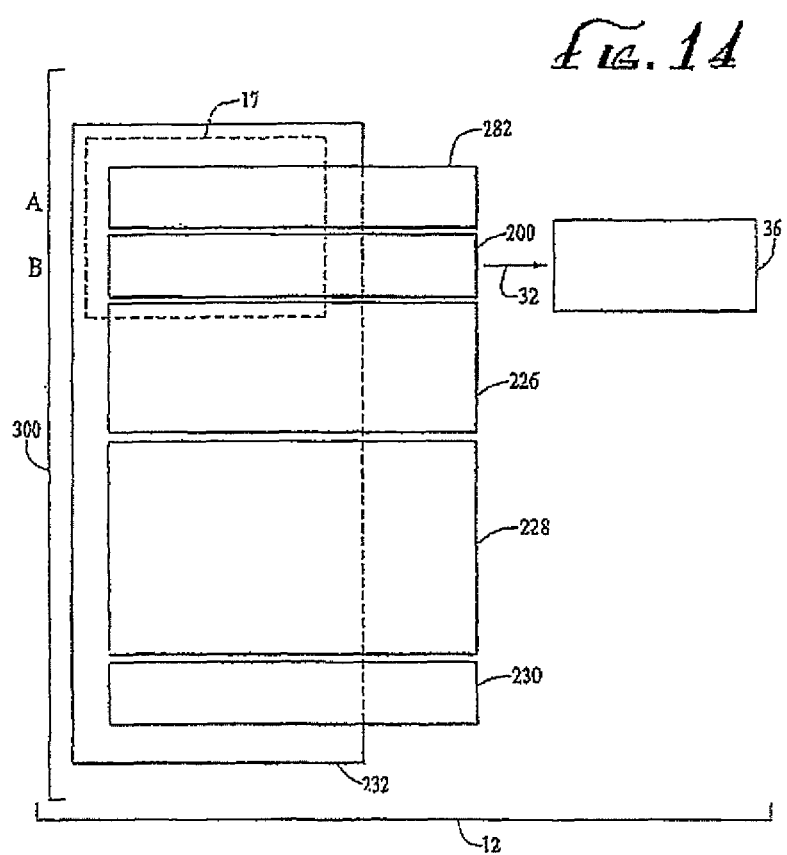
FIG. 14 is a schematic top view of an example of a flash luminescence cartridge system according to an embodiment of the present invention.

Referring now to FIG. 14, another embodiment of the invention, a flash luminescence cartridge system 300, for use in an apparatus 12 for analyzing a target in a sample (not shown) is provided. Measurement of flash type luminescence requires the injection of a starter reagent (or flash luminescence reagent), and measurement of luminescence light at a fraction of a second later. The configuration of the cartridge system 300 for this application has an injector cartridge 282, as described with respect to FIG. 13 and a luminescence cartridge 200 as described with respect to FIG. 9. The injector cartridge 282 and the luminescence cartridge 200 are positioned on adjacent slots on the cartridge support 232 as described with respect to FIG. 10. Any combination of cartridges may be possible (see for example FIG. 6). However, the cartridges are typically dedicated to a single (or only few) applications, unless the required performance would not be compromised by including an additional application. Preferably, due to the proximity of the injection position and the read position, the luminescence cartridge 200 and the injector cartridge 282 are fused into a single, dual slot cartridge.

As shown in FIG. 14, the luminescence cartridge 200 is aligned with the detector 36 and detects emitting light 32 from a first target 14a (not shown) on the sample support 17, which is positioned below the cartridge support 232. A flash type luminescence measurement is performed by first aligning the luminescence cartridge 200 with the detector 36 in the analysis position indicated in FIG. 14. The cartridge support 232 is then in a fixed position until the sample analysis is complete. The sample support 17 is then moved to align the first sample 16a (not shown) with the injector cartridge 282 in a first position, i.e., an "injecting position," position A. Starter reagent is then injected onto the first sample 16a. After the starter reagent is injected, the sample support 17 is then moved such that the first sample 16a on the sample support 17 is in a second position i.e., a "reading position," position B, where the first sample 16a is aligned with the luminescence read head (not shown) within the luminescence cartridge 200.

A measurement may be taken on a second sample 16b (not shown) by moving the sample support 17 to the injecting position, i.e., the "injecting position," position A, below the injector cartridge 282 and injecting starter reagent onto the second sample 16b. The sample support 17 is then moved such that the second sample 16b on the sample support 17 is in the second position i.e., the "reading position," position B, where the second sample 16b is aligned with the luminescence read head (not shown) within the luminescence cartridge 200.

According to another embodiment, the luminescence cartridge 900 described above and illustrated in FIG. 9A is utilized in the flash luminescence cartridge system 300, in place of the luminescence cartridge 200. In some embodiments, the luminescence cartridge 900 and the injector cartridge 282 may be integrated together as a single, dual slot cartridge. The flash luminescence cartridge system 300 may be operated with the luminescence cartridge 900 in generally the same manner as described above and illustrated in FIG. 14 in connection with the luminescence cartridge 200. However, the luminescence cartridge 900 includes an integrated luminescence detector 908 (FIG. 9A) instead of a separate read head 202 and external output detector 36 (FIG. 9), the luminescence cartridge 900 does not need to be aligned with the output detector 36. For each sample 16 being interrogated, the sample carrier 54 is simply moved to the injection position A to align the sample 16 with the injector cartridge 282 and inject the starter reagent, and then moved to the reading position B to align the sample 16 with the luminescence detector 908 and take the luminescence measurements for that particular sample 16.

Figure 15A:
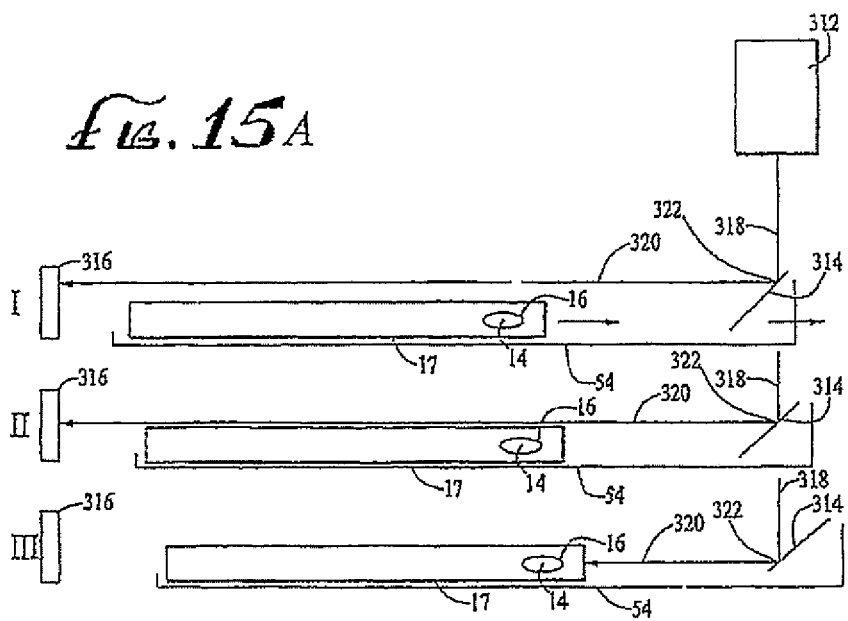
FIGS. 15A and 15B are schematic views of an example of a system for detecting the sample support clearance in a cartridge according to an embodiment of the present invention.
Figure 15B:
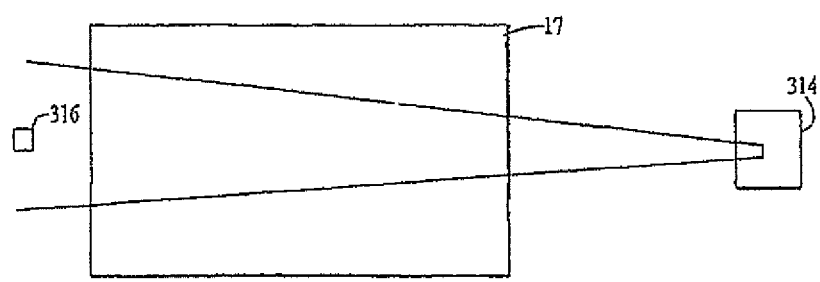

According to another preferred but not required embodiment of the invention, a sample support detector 310, for use in a system for analyzing a target 14 in sample 16 is shown in FIGS. 15A and 15B. As shown in FIG. 15A, a side view of the sample support detector 310, and FIG. 15B, a top view of the sample support detector 310, the sample support detector 310 comprises a detecting light source 312 (e.g., a laser pointer), a reflector 314 (e.g., a mirror) and a detector 316 (e.g., a photodiode). The sample support detector 310 measures the clearance (i.e., height) of the sample support 17 to avoid the luminescence read head or a fluorescence read head, which, when seeking to receive maximum signal from a sample may be moved down too far and thus collide with the top of the sample support 17. The result of the measurement produced by the sample support detector 310, is a value that instructs the software of the apparatus not to move lower than the particular value determined by the measurement.

According to the embodiment shown in FIGS. 15A and 15B, the detecting light source 312 produces a light beam 318, such as a laser line from a laser pointer, which is directed in the direction of the sample support 17. The reflector 314 is attached to the sample support carrier 54. Before reading the sample 16, the sample support carrier 54 is loaded with a sample 16 positioned on a sample support 17 outside the apparatus in a sample support loading position. To acquire a sample reading, the sample support carrier 54 must be retracted into the apparatus. On its way from the sample support loading position, outside the apparatus, to an inside initialization position, the sample support carrier 54 passes the detecting light source 312. Then, the light beam 318 is inflected (i.e., redirected) by the reflector 314 to produce an inflected light beam 320, which is parallel to the surface of the sample support 17, and then contacts the detector 316, as shown in FIG. 15A, view I. Then, the reflector 314 is moved such that the inflection point 322 of the light beam 318 on the reflector 314 moves down along the reflector surface until the inflected light beam 320 comes closer to the surface of the sample support 17, as shown in FIG. 15A, view II, and is further moved until the inflected light beam 318 is obstructed by the edge of the sample support 17, as shown in FIG. 15A, view III.

Preferably, as shown in FIG. 15A, the detecting light source 312 is positioned perpendicular to the sample support 17 and the reflector 314 redirects the light beam 318 at an angle of about 45 degrees so the inflected light beam 320 is approximately parallel to the sample support 17. Consequently, the signal at the photodiode undergoes an ON/OFF transition. By calibration using sample supports of different height, the position of the sample support 17 where the ON/OFF transition occurs is a measure of the height of the sample support 17.

As shown in FIG. 15B, alignment may be made less demanding by using a laser line pointer for the light beam 318 and projecting a fan of rays parallel to the surface of the sample support 17. The photodiode's sensitive area is extended in the direction orthogonal to the laser line projection (shown in FIG. 15B as vertical). Thereby, when not yet obstructed by the sample support 17, the fan of rays always has an intersection with the light detector 316.

Referring again to FIG. 5, according to another embodiment of the present invention, a method for fluorescence measurement using photoactivation of a functional group associated with a target 14 in a sample 16, the functional group being capable of changing from an inactivated state to an activated state in response to an exciting light is provided. According to this embodiment, first, a dual excitation cartridge 130 having first and second exciting light sources 116 and 18, respectively, which are capable of producing first and second exciting lights 118 and 20, respectively, is selected. Then, the first exciting light 118 is directed to the functional group associated with the target 14 in the sample 16, followed by directing the second exciting light 20 to the functional group associated with the target 14 in the sample 16. An emitting light 32 from the functional group associated with the target 14 is produced, and the emitting light 32 is directed to the detector 36 via the read head 28 and second optical system 34 in the cartridge 130. A signal that corresponds to the emitting light 32 is produced by the apparatus 12. A read-out may also be produced by the apparatus 12 which may be in a hard-copy or electronic form.

According to another embodiment of the present invention, a method for analyzing a target in a sample is provided. According to this embodiment, a cartridge system having a cartridge support and one or more cartridges that are removably engaged with a cartridge support is selected. The cartridges may be one or more of the cartridges described herein. Then, a first cartridge contained within the cartridge system is selected. A second cartridge, i.e., a new or replacement cartridge, not contained within the cartridge system is then selected. The first cartridge is then replaced with the second cartridge and a target in a sample is analyzed with the second cartridge. Preferably, the first cartridge may be removed from the apparatus and replaced with the second cartridge without the use of mechanical tools, and after the first cartridge is replaced with the second cartridge, the system is instructed, with apparatus-readable instructions, with information for analyzing the target in the sample.

According to another embodiment of the present invention, a method for analyzing a target in a sample or multiple samples is provided. According to this embodiment, first a cartridge system comprising first and second removable cartridges is selected. The first and second cartridges have one or more light sources that produce an exciting light, the exciting light produced from the first cartridge having a first wavelength, and the exciting light from the second cartridge having a second wavelength, the first and second wavelengths being different; and one or more supports configured to receive the first and second removable cartridges and align at least one of the removable cartridges with the detector and the read head. Then, a first sample to be analyzed is selected by aligning the first cartridge with the first sample, the detector, and read head. Preferably this is done by selecting the first cartridge and aligning the first cartridge with the read head and detector and then moving the first sample into an aligned position with the first cartridge. Then, the exciting light from the first cartridge is directed to the first target via the read head and a first emitting light from the first target is produced. The first emitting light from the first target is then directed to the detector and a first signal that corresponds to the first emitting light is produced. Then, the second cartridge is aligned with the first sample, the detector, and the read head. Preferably this is done by selecting the second cartridge and aligning the second cartridge with the read head and detector and then moving the first sample into an aligned position with the second cartridge. Then, the exciting light from the second cartridge is directed to the first target via the read head and a second emitting light from the first target is produced. The second emitting light from the first target is then directed to the detector and a second signal that corresponds to the second emitting light is produced. Preferably, the first and second emitting lights are directed from the first target to the detector via the read head and the first cartridge and second cartridge, respectively. The apparatus can also produce a read-out, such as a printed "hard copy" or electronic data of the first and second signals.

According to another embodiment, the method for analyzing a target in a sample or multiple samples further comprises analyzing a second target in a second sample, the second target being capable of generating third and fourth emitting lights in response to the exciting lights of the first and second wavelength. According to this embodiment, a second sample to be analyzed is selected. Then, the first cartridge is aligned with the second sample, the detector, and the read head, as previously described. Then, the exciting light from the first cartridge is directed to the second target via the read head and a third emitting light from the second target is produced. The third emitting light from the second target is then directed to the detector and a third signal that corresponds to the third emitting light is produced. The second cartridge is then aligned with the second sample, the detector, and the read head. The exciting light from the second cartridge is directed to the second target via the read head and a fourth emitting light from the second target is produced. The fourth emitting light is then directed from the second target to the detector and a fourth signal that corresponds to the fourth emitting light is produced. A read-out of the third and fourth signals may also be produced by the apparatus, as previously described, and/or a combined read-out of the first, second, third and fourth signals may be produced by the apparatus.

In the method described above, the order of sample analysis described as the first sample is initially analyzed by the first cartridge and then the second cartridge, and then the second sample is subsequently analyzed by the first cartridge and then the second cartridge. However, the invention is not limited to the order of sample analysis described above, as will be understood by those of skill in the art by reference to this disclosure. Further, for time saving in sample analysis, it is preferable to align the first cartridge with the detector and read head and complete the analysis of all the samples using the first cartridge in sequence, by moving the position of the samples relative to the first cartridge, such as by moving the samples on a microplate scanning stage. After all the samples have been analyzed with the first cartridge, the second cartridge may then be aligned with the detector and read head and the same, or additional samples may be analyzed.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 74 schematically depicted in FIGS. 2 and 9A. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 74 in FIGS. 2 and 9A), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A system for analyzing a target in a sample, the system comprising:
an apparatus housing;
a power source disposed in the apparatus housing;
a sample carrier disposed in the apparatus housing;
a cartridge support movable relative to the apparatus housing and comprising a plurality of cartridge positions configured for receiving a plurality of removable cartridges concurrently; and
a luminescence cartridge removably mounted at one of the cartridge positions, the luminescence cartridge comprising:
a cartridge housing having an opening;
a driver disposed in the cartridge housing and communicating with the power source; and
a luminescence detector communicating with the power source and coupled to the driver, wherein the luminescence detector is movable by the driver through the opening and alternately toward and away from the sample carrier,
wherein the sample carrier is movable for aligning the sample with the luminescence detector.

2. The system of claim 1, wherein the luminescence detector comprises an iris configured for adjusting a numerical aperture of the luminescence detector.

3. The system of claim 2, comprising an iris controller disposed in the apparatus housing and configured for transmitting control signals to the iris.

4. The system of claim 1, wherein the luminescence cartridge comprises a first electrical connector, the cartridge support comprises a second electrical connector to which the first electrical connector is removably coupled to when the luminescence cartridge is removably mounted at the cartridge position, and the driver and the luminescence detector communicate with the power source via the first electrical connector and the second electrical connector.

5. The system of claim 1, comprising signal processing circuitry disposed in the apparatus housing and configured for receiving detection signals from the luminescence detector.

6. The system of claim 5, wherein the luminescence cartridge comprises a first electrical connector, the cartridge support comprises a second electrical connector to which the first electrical connector is removably coupled to when the luminescence cartridge is removably mounted at the cartridge position, and the luminescence detector communicates with the signal processing circuitry via the first electrical connector and the second electrical connector.

7. The system of claim 1, comprising a drive controller disposed in the apparatus housing and configured for transmitting control signals to the driver.

8. The system of claim 7, wherein the luminescence cartridge comprises a first electrical connector, the cartridge support comprises a second electrical connector to which the first electrical connector is removably coupled to when the luminescence cartridge is removably mounted at the cartridge position, and the driver communicates with the drive controller via the first electrical connector and the second electrical connector.

9. The system of claim 1, comprising one or more additional cartridges removably mounted at one or more respective cartridge positions concurrently with the luminescence cartridge.

10. The system of claim 1, wherein the cartridge support configured for receiving the plurality of removable cartridges is a first cartridge support configured for receiving a plurality of first removable cartridges, and further comprising a second cartridge support configured for receiving a second removable cartridge, wherein the sample carrier is positioned between the first cartridge support and the second cartridge support.

11. The system of claim 10, wherein the second cartridge support comprises a plurality of cartridge positions configured for receiving a plurality of second removable cartridges concurrently.

12. The system of claim 1, comprising an injector cartridge removably mounted at one of the cartridge positions concurrently with the luminescence cartridge.

13. The system of claim 12, wherein the sample carrier is movable between an injecting position and a reading position, and wherein at the injecting position the sample is aligned with the injector cartridge and at the reading position the sample is aligned with the luminescence cartridge.

14. A method for analyzing a target in a sample, the method comprising:
providing the system of claim 1;
loading the luminescence cartridge on the cartridge support to position the luminescence cartridge in the apparatus housing;
moving the sample carrier supporting the sample, to align the sample with the luminescence detector;
moving the luminescence detector toward the sample until the luminescence detector has reached a desired distance to the sample; and
receiving luminescent light emitted from the sample at the luminescence detector.

15. The method of claim 14, wherein loading comprises moving the cartridge support at least partially outside the apparatus housing, and further comprising moving the luminescence cartridge into the apparatus housing by moving the cartridge support.

16. The method of claim 14, wherein loading comprises selecting one of the cartridge positions and removably mounting the luminescence cartridge at the selected cartridge position.

17. The method of claim 16, comprising loading an additional cartridge at another cartridge position, wherein the luminescence cartridge and the additional cartridge are loaded on the cartridge support concurrently.

18. The method of claim 14, wherein the cartridge support on which the luminescence cartridge is loaded is a first cartridge support, and further comprising loading an additional cartridge on a second cartridge support located at a side of the sample carrier opposite to the first cartridge support.

19. The method of claim 14, comprising providing power to a component of the luminescence cartridge from the power source, wherein the component is selected from the group consisting of an active detector component of the luminescence detector, an adjustable iris of the luminescence detector, the driver, and a combination of two or more of the foregoing.

20. The method of claim 14, comprising adjusting an iris of the luminescence detector to adjust a numerical aperture of the luminescence detector.

21. The method of claim 14, wherein loading comprises coupling a first electrical connector of the luminescence cartridge to a second electrical connector of the cartridge support.

22. The method of claim 14, wherein loading places the luminescence cartridge in signal communication with the power source, a system controller of the system, or both.

23. The method of claim 14, wherein loading places the luminescence cartridge in signal communication with a component of the system selected from the group consisting of a drive controller configured for moving the luminescence detector, an iris controller configured for adjusting an iris of the luminescence detector, signal processing circuitry configured for receiving a measurement signal from the luminescence detector, and a combination of two or more of the foregoing.

24. The method of claim 14, wherein moving the luminescence detector comprises transmitting a control signal from a system controller of the system to the driver.

25. The method of claim 14, comprising, after receiving luminescent light emitted from the sample, moving the sample carrier to align an additional sample supported by the sample carrier with the luminescence detector, and receiving luminescent light emitted from the additional sample.

26. The method of claim 14, wherein moving the sample carrier to align the sample with the luminescence detector comprises moving the sample carrier to a reading position, and further comprising (a) moving the sample carrier to an injecting position, (b) injecting a reagent into the sample, and (c) moving the sample carrier from the injecting position to the reading position at which luminescent light is received at the luminescence detector.

27. The method of claim 26, comprising repeating steps (a)-(c) one or more times to receive luminescent light emitted from one or more additional samples supported by the sample carrier.

28. The method of claim 26, further comprising loading an injector cartridge on the cartridge support such that the cartridge support supports the luminescence cartridge and the injector cartridge concurrently, wherein moving the sample carrier to the injecting position comprises aligning the sample with the injector cartridge.

* * * * *